(12) United States Patent
State et al.

(10) Patent No.: US 11,409,134 B2
(45) Date of Patent: Aug. 9, 2022

(54) ELECTROWETTING AND PHOTO CURING FOR MANUFACTURING OF OPHTHALMIC LENSES

(71) Applicant: AMO GRONINGEN B.V., Groningen (NL)

(72) Inventors: Mihai State, Groningen (NL); Theophilus Bogaert, Groningen (NL)

(73) Assignee: AMO Groningen B.V., Groningen (NL)

( * ) Notice: Subject to any disclaimer, the term of this patent is extended or adjusted under 35 U.S.C. 154(b) by 278 days.

(21) Appl. No.: 15/955,592

(22) Filed: Apr. 17, 2018

(65) Prior Publication Data

US 2018/0307061 A1  Oct. 25, 2018

Related U.S. Application Data

(60) Provisional application No. 62/487,128, filed on Apr. 19, 2017.

(51) Int. Cl.
| | |
|---|---|
| *G02C 7/08* | (2006.01) |
| *G02B 13/14* | (2006.01) |
| *G02B 26/00* | (2006.01) |
| *A61F 9/00* | (2006.01) |
| *G02C 7/02* | (2006.01) |
| *G02C 7/04* | (2006.01) |

(52) U.S. Cl.
CPC ............ *G02C 7/085* (2013.01); *A61F 9/0008* (2013.01); *G02B 13/14* (2013.01); *G02B 26/005* (2013.01); *G02C 7/022* (2013.01); *G02C 7/04* (2013.01); *A61F 2240/001* (2013.01)

(58) Field of Classification Search
None
See application file for complete search history.

(56) References Cited

U.S. PATENT DOCUMENTS

| | | |
|---|---|---|
| 6,936,196 B2 | 8/2005 | Chandross et al. |
| 7,126,903 B2 | 10/2006 | Feenstra et al. |
| 7,864,440 B2 | 1/2011 | Berge |
| 7,993,399 B2 | 8/2011 | Peyman |
| 8,348,424 B2 | 1/2013 | Pugh et al. |
| 8,460,376 B2 | 6/2013 | Donitzky et al. |
| 8,545,555 B2 | 10/2013 | Berge |
| 9,310,628 B2 | 4/2016 | Barre et al. |
| 2006/0072070 A1 | 4/2006 | Kuiper et al. |
| 2008/0117521 A1 | 5/2008 | Krupenkin et al. |
| 2008/0239502 A1* | 10/2008 | Immink ............... G02B 26/005 359/666 |

(Continued)

OTHER PUBLICATIONS

Partial International Search report for Application No. PCT/EP2018/059850, dated Jul. 11, 2018, 14 pages.

*Primary Examiner* — Ricky L Mack
*Assistant Examiner* — Journey F Sumlar
(74) *Attorney, Agent, or Firm* — Johnson & Johnson Surgical Vision, Inc.

(57) ABSTRACT

Apparatuses, systems, and methods for producing a lens surface through electrowetting. The lens surface may be used in an ophthalmic lens such as an intraocular lens, contact lens, or eyeglass lens. A fluid chamber may include a conductive fluid and a curable fluid positioned therein. An electrode may be used to vary a shape of a surface of the curable fluid through electrowetting. The surface of the curable fluid may be cured to produce a lens surface.

17 Claims, 13 Drawing Sheets

(56) References Cited

U.S. PATENT DOCUMENTS

| | | |
|---|---|---|
| 2010/0149651 A1 | 6/2010 | Berge et al. |
| 2012/0075712 A1 | 3/2012 | Pugh et al. |
| 2012/0092612 A1 | 4/2012 | Binder |
| 2012/0133064 A1* | 5/2012 | Newman ................ B29C 41/34 |
| | | 264/1.36 |
| 2014/0081396 A1 | 3/2014 | Maillard et al. |
| 2016/0070038 A1* | 3/2016 | Peyman ................ A61F 2/1635 |
| | | 359/666 |
| 2020/0099861 A1* | 3/2020 | Wayne ............... H04N 5/23212 |

* cited by examiner

ELECTROWETTING AND PHOTO CURING FOR MANUFACTURING OF OPHTHALMIC LENSES

CROSS-REFERENCES TO RELATED APPLICATIONS

This application claims the benefit of U.S. Provisional Patent Application No. 62/487,128, filed Apr. 19, 2017, which is incorporated herein by reference in its entirety.

BACKGROUND

Intraocular lenses may be used for correcting aphakia after cataract surgery. During surgery the clouded crystalline lens is removed and replaced by an intraocular lens usually made from a transparent optical elastomer often based on silicone or acrylic polymers. From a physical point of view, intraocular lenses are often produced with different additives such as chromophores to absorb UV and near UV blue filter to protect the retina.

Intraocular lenses are often made available in the lens power range of 5.0 D-34.0 D with power increments of 0.5 D. However, some patients may require a lens power down to −15 D or up to 40 D depending on the axial length of their eye and/or the corneal refraction. Many cataract patients may also have refractive errors in their cornea of which spherical aberration and astigmatism are the most prevailing. Astigmatism correction may be enabled by intraocular lenses in steps of 0.75 D and up to 9.0 D. Taking into account the entire optical power range, the number of combinations may reach 110 (lens power)×12 (cylinder power)=1320 products. If multifocal intraocular lenses are included and a variety in add power is taken into account (0 D to 4 D in increments of 0.5) plus any need for 0.25 D optic power increments, this number may be 16 times higher: 21120 products. In addition, lenses can be made with a range of spherical aberration corrections ranging from positive spherical aberration to negative spherical aberration. In addition, the lenses can be made from different materials such as silicone and hydrophilic and hydrophobic acrylic polymers.

The variety of intraocular lenses represents a number of unique intraocular lenses that may be difficult to keep on stock or in consignment by an optical practitioner. Ideally, the optical practitioner should select a lens that is exactly conforming to the biometric and lifestyle needs of a given patient. In this case, the potential number of unique products may approximately equal the total number of patients.

A variety of manufacturing methods are available for intraocular lenses: reaction molding by thermo curing or photo curing, injection molding, and (Cryo) lathe cutting, are commonly used.

However, it may be difficult for these manufacturing methods to be quickly and easily performed to produce an intraocular lens tailored for the needs of a patient. In addition, it may be difficult for these manufacturing methods to be performed locally with an optical practitioner such as an ophthalmologist performing or preparing a cataract surgery procedure. These issues may be present not only with intraocular lenses, but also with other forms of ophthalmic lenses such as contact lenses or eyeglass lenses.

SUMMARY

Apparatuses, systems, and methods are disclosed herein that utilize the principle of electrowetting to shape a lens surface. The electrowetting process may provide an efficient manner of shaping and producing a lens surface for use in an ophthalmic lens, such as an intraocular lens, contact lens, or eyeglass lens. Methods may be performed locally with an optical practitioner.

The optical practitioner may be able to perform an assessment of the desired properties of a lens for a patient and determine the desired optical properties of a lens for a patient in terms of lens power, cylinder power, add power, asphericity, or any desired higher order aberrations, among others. The optical practitioner may be able to produce a custom lens for the patient locally with desired properties such as UV and visible light transmittance, base polymer, or others. This feature may beneficially allow an optical practitioner to readily produce a lens that meets the needs of a patient, and may reduce the number of lenses the practitioner keeps on stock or in consignment. Other methods may be used for large-scale or factory manufacturing.

In one embodiment, a system is disclosed including a fluid chamber having an interior surface. A conductive fluid is positioned in the fluid chamber and contacts the interior surface at a contact angle. A curable fluid is positioned in the fluid chamber and is immiscible with the conductive fluid. The curable fluid has a surface with a shape, the surface of the curable fluid facing the conductive fluid, and the shape of the surface of the curable fluid being dependent on the contact angle of the conductive fluid with the interior surface. One or more electrodes are configured to vary a voltage between the conductive fluid and at least one of the one or more electrodes to thereby vary the contact angle and the shape of the surface of the curable fluid.

In one embodiment, a method is disclosed including providing a fluid chamber having an interior surface, the fluid chamber including a conductive fluid and a curable fluid therein, the curable fluid having a surface that faces the conductive fluid and that has a shape. The method includes varying the shape of the surface of the curable fluid by varying a wettability of the interior surface. The method includes at least partially curing the curable fluid. The at least partial curing of the curable fluid may include converting it into a polymer capable of maintaining its shape without the fluid chamber.

In one embodiment, a method is disclosed including providing a fluid chamber that is positioned upon at least a portion of an intraocular lens, the fluid chamber including a conductive fluid and a curable fluid therein, the conductive fluid and the curable fluid being immiscible and being separated at an interface, the curable fluid being in contact with at least the portion of the intraocular lens. The method includes varying a shape of the interface by varying a voltage between the conductive fluid and one or more electrodes. The method includes at least partially curing the curable fluid when the curable fluid is in contact with the at least the portion of the intraocular lens.

BRIEF DESCRIPTION OF THE DRAWINGS

Features and advantages of the systems, apparatuses, and methods as disclosed herein will become appreciated as the same become better understood with reference to the specification, claims, and appended drawings wherein:

DETAILED DESCRIPTION

Figure 1:
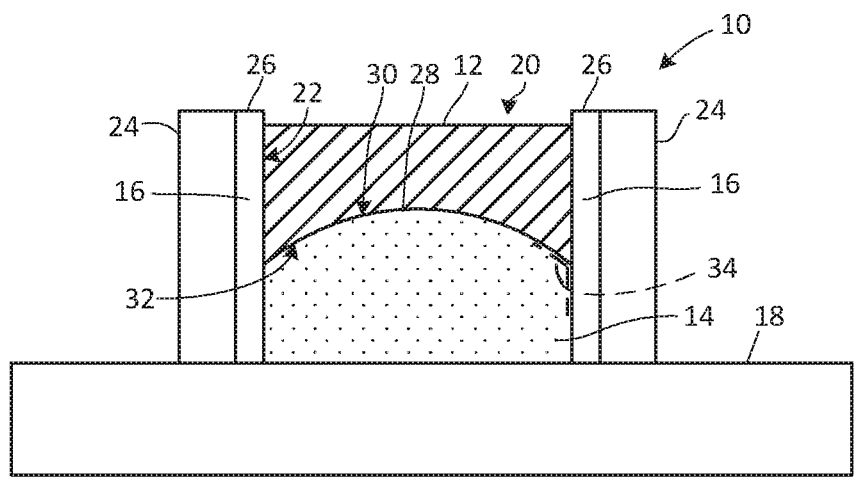
FIG. 1 illustrates a side cross sectional view of a fluid chamber according to an embodiment of the present disclosure.

FIG. 1 illustrates a side view of an embodiment of a fluid chamber 10 according to an embodiment of the present disclosure. The fluid chamber 10 includes a curable fluid 12 and a conductive fluid 14 positioned therein.

The fluid chamber 10 includes walls 16, 18 that define a cavity 20. A side wall 16 extends around the cavity 20. An end wall 18 is positioned at the bottom of the cavity 20 and bounds the bottom of the fluid chamber. The walls 16, 18 enclose the cavity 20. The cavity 20 is for receiving the curable fluid 12 and the conductive fluid 14.

An interior surface 22 of the fluid chamber 10 faces the cavity 20. The interior surface 22 forms the interior surface of the side wall 16 and the end wall 18. In one embodiment, the interior surface 22 may form a portion of one or more of the side wall 16 and/or end wall 18.

The interior surface 22 of the side wall 16 may have a cylindrical shape such that the cavity 20 has a corresponding cylindrical shape. In other embodiments, the interior surface 22 of the side wall 16 may have a rectangular, elliptical, or other shape as desired, with the cavity 20 having a corresponding rectangular, elliptical, or other shape.

The side wall 16 may include an electrode 24. The electrode 24 may be configured to apply an electric field to the conductive fluid 14 positioned in the cavity. The electrode 24 may have a cylindrical shape and may extend around the cavity 20. In other embodiments, the electrode 24 may have a rectangular, elliptical, or other shape as desired, which may match the shape of the cavity 20. In other embodiments, the electrode 24 may comprise multiple electrodes.

The side wall 16 may include an insulator layer 26. The insulator layer 26 may be positioned between the electrode 24 and the fluids 12, 14 in the cavity 20. The insulator layer 26 may have a cylindrical shape to extend around the cavity 20 and cover the electrode 24. In other embodiments, the insulator layer 26 may have a rectangular, elliptical, or other shape as desired, which may match the shape of the cavity 20. The insulator layer 26 may comprise a dielectric or other form of insulator.

The insulator layer 26 may be made out of hydrophobic material or may include a hydrophobic coating that faces the cavity 20. The hydrophobic coating may be positioned between the insulator layer 26 and the fluids 12, 14 in the cavity 20. The hydrophobic coating may serve to reduce hysteresis and may enhance the contact angle of the conductive fluid 14 with the interior surface 22.

The electrode 24 may be separated from the conductive fluid 14 by the insulator layer 26 and the hydrophobic coating. In other embodiments, the insulator layer 26 or the hydrophobic coating may be removed and the electrode 24 may be in direct contact with the conductive fluid 14.

In other embodiments, the electrode 24 may not be part of the side wall 16, and may be positioned in a different location in relation to the cavity 20.

The fluid chamber 10 is configured to hold the curable fluid 12 and the conductive fluid 14. The fluid chamber 10 may have an open upper end, as shown in FIG. 1, or in other embodiments may be sealed.

The curable fluid 12 is fluid that may be cured. The curable fluid 12 may be cured by processes including thermo curing or photo curing, combinations of thermo curing and photo curing, or other forms of curing. The curable fluid 12 may be cured to produce a lens or a portion of a lens, which may be used for ophthalmic purposes. The curable fluid 12 may result in an elastomeric material for use as an ophthalmic lens such as a contact lens or an intraocular lens.

The curable fluid 12 may be cured through polymerization. The polymerization process may occur through thermo curing or through photo curing, combinations of thermo curing and photo curing, or other forms of curing. In an embodiment in which the curable fluid 12 is cured through photo curing, the curable fluid 12 may include monomers, oligomers, macromolecules, photo initiators, and combinations thereof. In one embodiment, a mixture of monomers, oligomers or macromolecules, and photo initiators, may be used. In one embodiment, other curable materials may be used as a curable fluid. The curing process may occur through exposure of the curable fluid 12 to light, which may comprise ultraviolet (UV) light, visible light (e.g., blue light), or light with other wavelengths or electromagnetic radiation with other wavelengths (herein referred to as "light"). The curable fluid may also contain additives to control the reaction such as chain transfer agents.

The curable fluid 12, when cured, may ultimately result in a silicone or acrylic polymer, or other form of polymer. In other embodiments, another material may result. The curable fluid 12 may include silicone or acrylic monomers to result in a silicone or acrylic polymer. A lens or lens portion with ultraviolet filtering or visible light filtering properties may result (e.g., UV filter or near UV blue filter).

The curable fluid 12 may be electrically insulating. In other embodiments, the curable fluid 12 may be electrically conductive.

The conductive fluid 14 is positioned in the fluid chamber 10 with the curable fluid 12. The conductive fluid 14 is electrically conductive. The conductive fluid 14 may be water or other polar fluid, or other electrically conductive fluid. In other embodiments, the conductive fluid 14 may be water containing electrolytes such as a saline solution, or another electrolytic solution. The conductive fluid 14 is preferably non-curable.

Both the curable fluid 12 and the conductive fluid 14 may be a liquid, which may include suspensions and solutions.

The curable fluid 12 is preferably immiscible with the conductive fluid 14.

The curable fluid 12 and the conductive fluid 14 are in contact with each other and are separated at an interface 28. The curable fluid 12 has a surface 30 that faces the conductive fluid 14 and is positioned at the interface 28. The conductive fluid 14 has a surface 32 that faces the curable fluid 12 and is positioned at the interface 28. The respective surfaces 30, 32 are formed due to the immiscible nature of the fluids 12, 14 and represent the boundary of the respective fluids 12, 14 towards each other.

The curable fluid 12 may have a lesser density than the conductive fluid 14, and may therefore be positioned above the conductive fluid 14, as shown in FIG. 1. In other embodiments, this configuration may be reversed such that the conductive fluid 14 is positioned above the curable fluid 12.

The conductive fluid 14 has a surface tension. The surface tension of the conductive fluid 14 results in the conductive fluid 14 contacting the surface 22 of the side wall 16 at an angle, referred to as the contact angle 34. The contact angle 34 is due in part to the surface tension of the conductive fluid 14 and the properties of the surface 22 of the side wall 16 at the interface between the conductive fluid 14 and the surface 22 of the side wall 16. The surface 22 of the side wall 16 has a certain wettability, which results in the contact angle 34 of the conductive fluid 14 with the surface 22. If a hydrophobic material or coating is in contact with the conductive fluid 14, this may reduce the wettability of the surface 22, and increase the contact angle 34.

A shape of the interface 28, and the shape of the respective surfaces 30, 32 of the fluids 12, 14, is dependent on the contact angle 34. A variation in the contact angle 34 will change the shape of the interface 28 to varying amounts of convexity, or concavity, or other shapes. As shown in FIG. 1, the contact angle 34 is relatively high and the interface 28 has a convex shape with respect to the conductive fluid 14. The surface 32 of the conductive fluid 14 similarly has a convex shape with respect to the conductive fluid 14. The surface 30 of the curable fluid 12 has a concave shape with the respect to the curable fluid 12.

The wettability of the surface 22, and the contact angle 34 may be varied through electrowetting. Electrowetting modifies the wettability of the surface 22 with an applied electric field. The contact angle 34 varies according to a variation in voltage between the conductive fluid 14 and the electrode 24. Accordingly, the shape of the interface 28, and the shape of the respective surfaces 30, 32 of the fluids 12, 14 varies according to a variation in voltage between the conductive fluid 14 and the electrode 24. As such, by controlling the voltage of the electrode 24, the shape of the respective surfaces 30, 32 of the fluids 12, 14 may be controlled.

Figure 2:
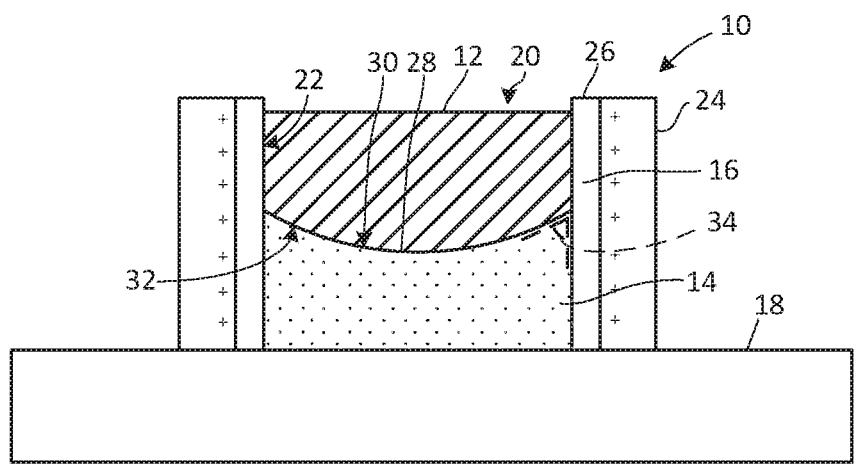
FIG. 2 illustrates a side cross sectional view of the fluid chamber shown in FIG. 1, with a variation in a voltage between an electrode and a conductive fluid.

A variation in the voltage between the conductive fluid 14 and the electrode 24 is shown in FIG. 2. The electrical potential of the electrode 24 has been varied, which results in a variation in the voltage between the conductive fluid 14 and the electrode 24. The wettability of the surface 22 has been varied, and accordingly the contact angle 34 of the conductive fluid 14 to the surface 22 has also been varied. The contact angle 34 has decreased from the angle shown in FIG. 1. The shape of the interface 28 has varied such that the interface 28 has a concave shape with respect to the conductive fluid 14. The surface 32 of the conductive fluid 14 similarly has a concave shape with respect to the conductive fluid 14. The surface 30 of the curable fluid 12 has a convex shape with the respect to the curable fluid 12.

Figure 7:
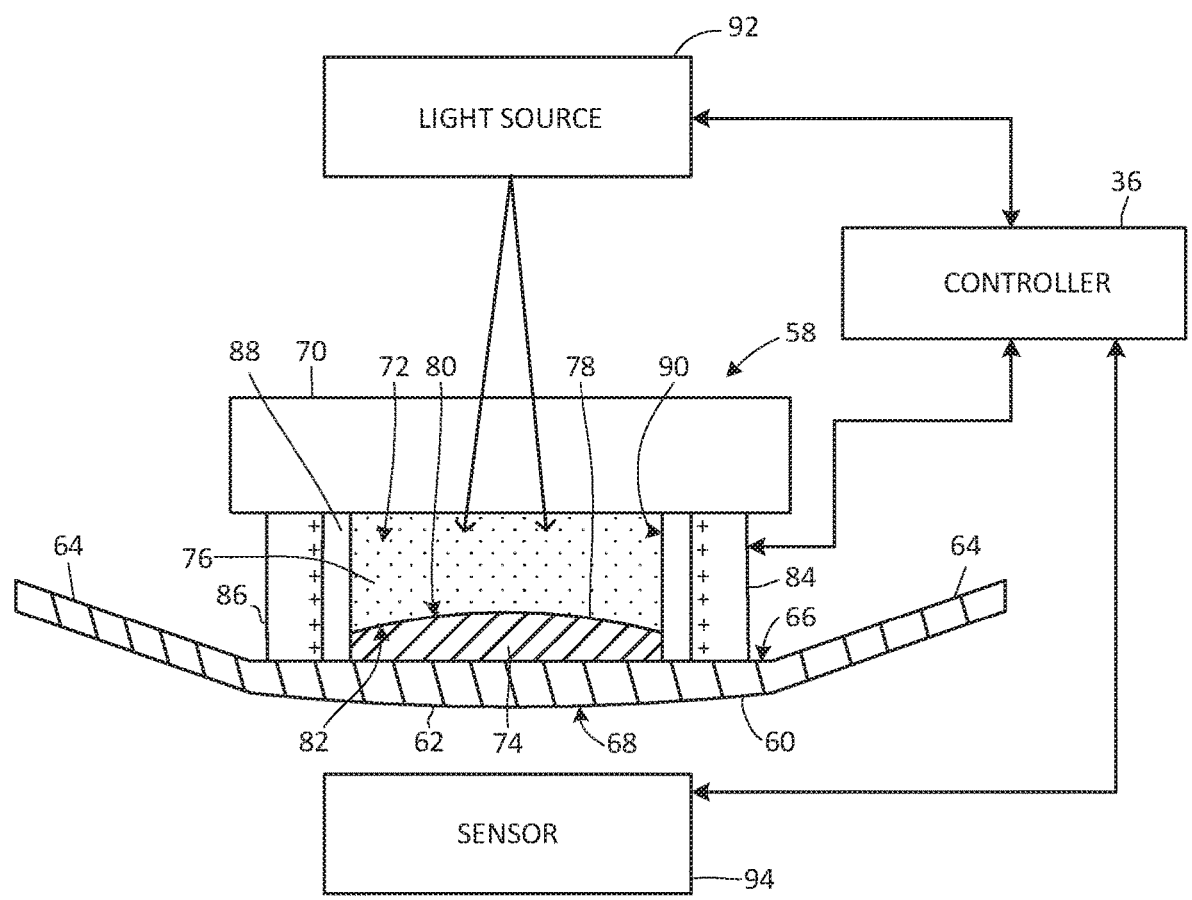
FIG. 7 illustrates a side cross sectional view of a fluid chamber positioned upon an intraocular lens base, according to an embodiment of the present disclosure.

The voltage difference between the conductive fluid 14 and the electrode 24 may be controlled to result in a desired shape of the interface 28. In one embodiment, a controller 36 as shown in FIG. 7 may be used to control the voltage between the conductive fluid 14 and the electrode 24 and accordingly may control the shape of the interface 28.

Control of the shape of the interface 28 may be used to control optical properties of a lens or portion of a lens that results from the curable fluid 12. The surface 30 of the curable fluid 12 may comprise a surface of a lens or portion of a lens. By varying the shape of the interface 28, the shape of the surface 30 of the curable fluid 12 may be varied, and accordingly, the shape of a surface of a resulting lens or portion of a lens may be varied as well. The shape of the surface 30 of the curable fluid 12 may be varied to result in a lens or portion of a lens having differing optical properties such as differing lens power, cylinder power, or other optical properties. As shown in FIGS. 1 and 2, the optical properties of the surface 30 may be varied from a lens having a negative optical power in FIG. 1 to a surface 30 of a lens having a positive optical power in FIG. 2.

The shape of the surface 30 of the curable fluid 12 may be varied to produce a desired shape. Upon the desired shape being formed, the curable fluid 12 may be cured or partially cured while the curable fluid 12 remains in the fluid chamber 10. The voltage between the conductive fluid 14 and the electrode 24 is preferably maintained during all or a portion of the curing process in order to maintain the shape of the surface 30 of the curable fluid 12 during curing.

In one embodiment, such as the embodiment shown in FIGS. 17-20, the voltage between the conductive fluid and the electrode may be varied during the curing process.

In an embodiment in which the curing process is thermal, the curing may occur by lowering or raising a temperature of the curable fluid 12. In one embodiment, the lens or portion of a lens may be heated and then cooled in a curing process. The curable fluid 12 may be heated to initiate the curing process and to harden the curable fluid 12 and form a lens or portion of a lens having desired optical properties. In one embodiment, the curable fluid 12 may be configured to be cooled to harden the curable fluid 12. The curable fluid 12 configured to be in a liquid state above a temperature such as 100 degrees Celsius. The curable fluid 12 may be cooled to a temperature below 100 degrees Celsius to cure the curable fluid 12. In other embodiments, other temperatures or methods may result in curing of the curable fluid 12.

In an embodiment in which the curing process involves photo curing, the curing may occur by applying light to the curable fluid 12. The light may be applied to the curable fluid 12 when the curable fluid 12 is in the fluid chamber 10. The light may be provided through the open upper end of the fluid chamber 10 to be applied to the curable fluid 12. In one embodiment, the end wall 18 may be configured to be optically transparent such that the light may be applied to the curable fluid 12 through the end wall 18. In one embodiment, the side wall 16 may be configured to be optically transparent such that the light may be applied to the curable fluid 12 through the side wall 16. In one embodiment, all or a portion of any of the walls 16, 18 may be optically transparent such that light may be applied to the curable fluid 12.

In the embodiment of FIGS. 1 and 2, the curing process results in a lens or portion of a lens having a one sided surface 30. The curing process may result in a lens or portion of a lens having an outer periphery shape that is formed by the shape of the interior surface 22 of the fluid chamber 10. For example, if the interior surface 22 of the fluid chamber 10 has a cylindrical shape, the outer periphery of the resulting lens or lens portion may have a cylindrical shape. In other embodiments, the outer periphery of the resulting lens or lens portion may be shaped by a separate process.

Figure 3:
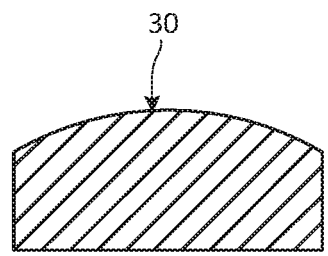
FIG. 3 illustrates a side cross sectional view of a lens surface produced from the fluid chamber shown in FIG. 1.

Upon the curable fluid 12 being cured or partially cured, the curable fluid 12 is removed from the fluid chamber 10. FIG. 3 illustrates a lens formed from the curable fluid 12 after it is removed from the fluid chamber 10 (and rotated 180 degrees). The surface 30 of the lens corresponds to the surface 30 of the curable fluid 12 shown in FIG. 2. The at least partial curing of the curable fluid 12 may produce a surface of a lens from the surface 30 of the curable fluid 12. The resulting lens or portion of a lens may be further cured, or may be finished for implementation as an ophthalmic lens. The finishing processes may include cleaning, polishing, coating, or providing further shaping of the ophthalmic lens.

In an embodiment in which the resulting lens or portion of a lens may be used for an intraocular lens, the resulting lens or portion of a lens may be bonded to an additional portion of an intraocular lens, which may include an intraocular lens base. The resulting lens or portion of a lens may be bonded to the intraocular lens base through adhesives or welding or other form of bonding. The resulting lens or portion of a lens may be connected to haptics or other structures designed for insertion into an individual's eye. Various types of base intraocular lenses may be utilized, including base intraocular lenses with haptics, without haptics, with haptics constructed into the material of the intraocular lens, and haptics not constructed into the material of the intraocular lens, among others. The resulting intraocular lens may comprise an accommodating intraocular lens for providing accommodating movement in the eye, or a monofocal or multifocal intraocular lens, or other form of intraocular lens. An opposing surface of the intraocular lens that the resulting lens or portion of a lens is not bonded to may comprise an optical surface such as a diffractive pattern, or optical zones, or other form of optical surface.

In an embodiment in which the resulting lens or portion of a lens may be used for a contact lens, the resulting lens or portion of a lens may be shaped or otherwise configured for use as a contact lens. In an embodiment in which the resulting lens or portion of a lens is used for an eyeglass lens, the resulting lens or portion of a lens may also be shaped or otherwise configured for use as an eyeglass lens. The resulting lens or portion of a lens may be affixed to an eyeglass frame.

In one embodiment, the conductive fluid 14 may not be utilized. In this embodiment, the curable fluid 12 would preferably have some amount of electrical conduction, such that a shape of a surface of the curable fluid would be affected by the electrowetting process. The shape of the surface of the curable fluid 12 may be modified in the same manner that the shape of the surface of the conductive fluid 14 is modified.

Figure 4:
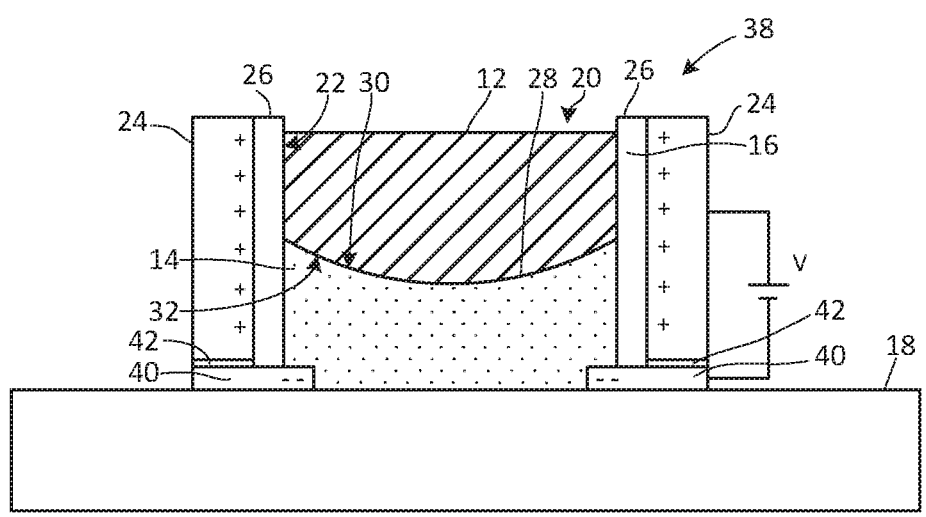
FIG. 4 illustrates a side cross sectional view of a fluid chamber according to an embodiment of the present disclosure.

FIG. 4 illustrates a side view of an embodiment of a fluid chamber 38 including an additional electrode 40 positioned interior of the side wall 16. The electrode 40 may be positioned to apply an electrical potential to the conductive fluid 14 and to enhance a voltage difference between the conductive fluid 14 and the electrode 24. As such, a voltage difference between the conductive fluid 14 and at least one of the two electrodes 24, 40 results in a variation in the shape of the surface 30 of the curable fluid 12. The electrode 40 may additionally allow a user to better control the voltage difference between the conductive fluid 14 and the electrode 24.

The electrode 40 may be positioned at an end of the fluid chamber 38, for example a bottom end as shown in FIG. 4. The electrode 40 may be positioned near the surface 22 of the side wall 16 and may have an annular shape. The annular shape of the electrode 40 may allow the electrode 40 to contour to a cylindrical shape of the surface 22 of the side wall 16. In an embodiment in which the surface 22 of the side wall 16 has a different shape, the electrode 40 may have a shape that contours to the shape of the surface 22.

An insulator layer 42 may be positioned between the electrode 40 and the electrode 24, to provide electrical insulation between these electrodes 24, 40.

In other embodiments, one or more of the electrodes 24, 40 may have a different shape or position as desired. In one embodiment, one of the electrodes 24, 40 may form a bottom plate electrode upon which the conductive fluid 14 is positioned. The bottom plate electrode may be variably charged to vary a contact angle of the conductive fluid 14 with the surface of the bottom plate electrode. The shape of the interface 28 may be modified by varying the voltage between the conductive fluid 14 and the bottom plate electrode. In a variation of this embodiment, the conductive fluid 14 may not be utilized, and the curable fluid 12 having some amount of electrical conduction may be positioned on the bottom plate electrode, to vary the shape of a surface of the curable fluid 12 and produce a desired lens surface shape.

The varied electrode shape, position, and configuration disclosed in regard to FIG. 4, including use of additional electrode(s) interior of the fluid chamber cavity to produce a desired lens shape, may be incorporated into any embodiment of fluid chamber disclosed in this application.

Figure 5:
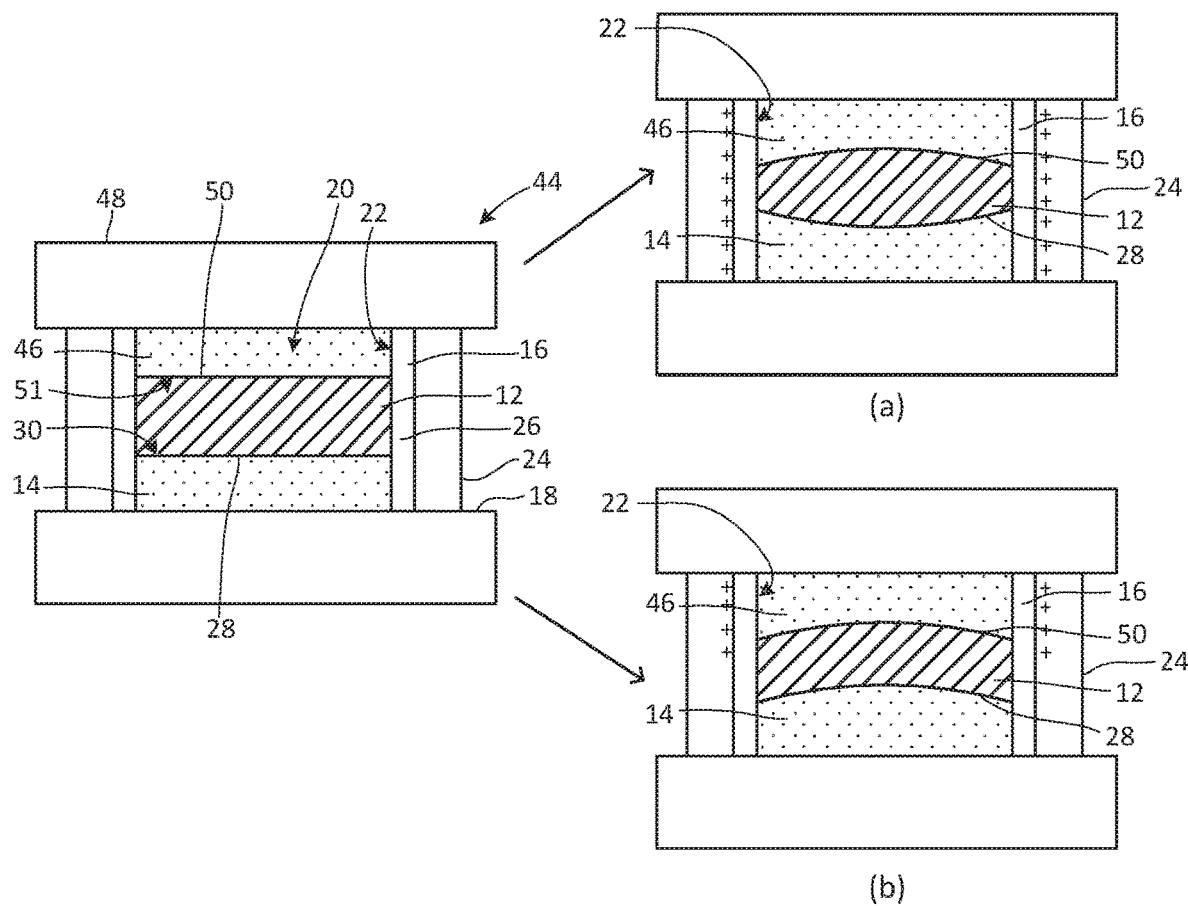
FIG. 5 illustrates a side cross sectional view of a fluid chamber according to an embodiment of the present disclosure, with two alternative results (a) and (b).

FIG. 5 illustrates a side view of an embodiment of a fluid chamber 44 in which an additional conductive fluid 46 is positioned above the curable fluid 12. The curable fluid 12 may be sandwiched between the lower conductive fluid 14 and the upper conductive fluid 46. The curable fluid 12 and the conductive fluids 14, 46 may be selected such that the lower conductive fluid 14 has a higher density than the curable fluid 12, which in turn has a higher density than the upper conductive fluid 46. The upper conductive fluid 46 may be immiscible with the curable fluid 12 to form an interface 50 between the upper conductive fluid 46 and the curable fluid 12.

The fluid chamber 44 may additionally include an end wall 48 positioned at the top of the cavity 20. The top end wall 48 and the bottom end wall 18 may seal the cavity 20. In one embodiment, either or both of the end walls 48, 18, may be made of a flexible membrane to allow shrinkage of the curable fluid 12 during curing. In one embodiment, a reservoir of conductive fluid may be provided to allow the curable fluid 12 to shrink without the introduction of tension stress in the material due to the creation of an under pressure in the fluid chamber 44. It is preferred that tension stresses are avoided as they can result in stress deformation and/or shrink marks in the resulting lens or portion of a lens.

The fluid chamber 44 may be configured to allow for shaping of the lower interface 28, between the curable fluid 12 and the lower conductive fluid 14, as well as shaping of the upper interface 50 between the curable fluid 12 and the upper conductive fluid 46, both via electrowetting. The curable fluid 12 has a surface 30 that faces the lower conductive fluid 14 and a surface 51 that faces the upper conductive fluid 46. The fluid chamber 44 may allow for different shapes of the lens surfaces that result from the curable fluid 12.

The fluid chamber 44 may have the lower interface 28 take a convex shape with respect to the curable fluid 12, and may have the upper interface 50 take a convex shape with respect to the curable fluid 12 as well. The curable fluid 12 may result in a lens or portion of a lens that is bi-convex. Result (a) of FIG. 5, for example, illustrates the lower interface 28 and upper interface 50 both taking a convex shape to result in a bi-convex lens.

In one embodiment, the fluid chamber 44 may have the lower interface 28 take a concave shape with respect to the curable fluid 12, and may have the upper interface 50 take a convex shape with respect to the curable fluid 12. The curable fluid 12 may result in a lens or portion of a lens that has a meniscus shape. Result (b) of FIG. 5, for example, illustrates the lower interface 28 taking a concave shape and the upper interface 50 taking a convex shape to result in a meniscus lens.

The shapes of the lower interface 28 and the upper interface 50 may be varied as desired. Either or both interfaces 28, 50 may be made to have varying amounts of convexity or concavity, or other shape, such as planar. The contact angles of the lower conductive fluid 14 and the upper conductive fluid 46 with the interior surface 22 of the side wall 16 may be varied as desired. Varying the shapes of the interfaces 28 results in corresponding varied shapes of the surfaces 30, 51 of the curable fluid 12.

To vary the shape of the interfaces 28, 50, the electrode 24 may be charged to provide the corresponding shape of the interface 28, 50. For example, in result (a) of FIG. 5, the entirety of the electrode 24 may be charged to increase the wettability of the entirety of the surface 22 of the side wall 16. The increased wettability of the surface 22 may decrease the contact angle of both the lower conductive fluid 14 and the upper conductive fluid 46 with the surface 22 of the side wall 16.

In result (b) of FIG. 5, a portion of the electrode 24, for example, an upper portion, may be charged to increase the wettability of a portion of the surface 22 of the side wall 16. The increased wettability of the upper portion of the surface 22 of the side wall 16 may decrease the contact angle of the upper conductive fluid 46 with the surface 22 of the side wall 16.

In other embodiments, the electrode 24 may be segmented into a plurality of electrodes to vary the voltage difference between the upper conductive fluid 46 and the lower conductive fluid 14, and the plurality of electrodes, in a desired geometry. The segmented electrodes may form a variety of shapes, including an annular array around the cavity of the fluid chamber. The control of the electrode voltages may occur through a variety of methods. Such methods may include amplitude modulation and/or phase and/or time delays, which may control the electrical excitation of individual electrodes to enable a better end-surface shape control or to generate lens surfaces with a higher relative degree of complexity, such as (high order) aspheres, and tori. Methods may include varied electrical amplitude pulses in time and space to the various electrodes.

The curable fluid 12 may be cured in a similar manner as discussed in regard to the embodiment shown in FIGS. 1-4. The curable fluid 12 may be thermo or photo cured, or a combination of thermo and photo curing, in a similar manner as described in regard to FIGS. 1-4. In an embodiment in which the curable fluid 12 is photo cured, all or a portion of any of the walls 16, 18, 48 may be optically transparent such that light may be applied to the curable fluid 12.

In one embodiment, a controller 36 as shown in FIG. 7 may be used to control the voltage between the conductive fluid 14 and the electrode 24 in a desired manner, and accordingly may control the shape of the interfaces 28, 50.

In one embodiment, additional electrode(s), such as the additional electrode shown in regard to FIG. 4 may be utilized, such that they are positioned interior of the fluid chamber cavity. The electrode(s) may be positioned adjacent to the respective walls 18, 48 to produce a desired shape of the respective interface 28, 50.

Figure 6:
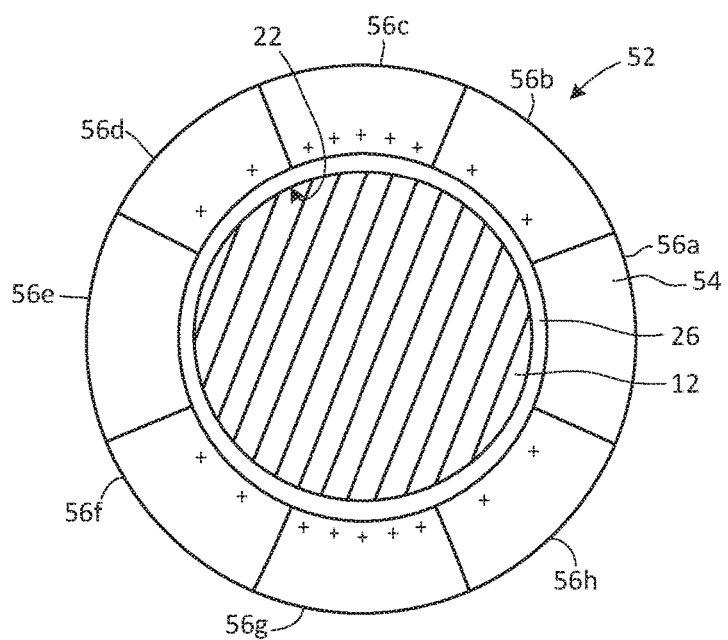
FIG. 6 illustrates a top view of a fluid chamber according to an embodiment of the present disclosure.

FIG. 6 illustrates a top view of a fluid chamber 52 in which the side wall 54 includes a plurality of electrodes 56a-56h. The fluid chamber 52 may have a similar geometry as the fluid chambers discussed in regard to FIGS. 1-5, in that the interior surface 22 of the fluid chamber 52 has a cylindrical shape. The insulating layer 26 may be positioned between the plurality of electrodes 56a-56h and the curable fluid 12 in a similar manner as discussed in regard to the fluid chamber 10 of FIG. 1.

The plurality of electrodes 56a-56h may be configured to have different voltages between the electrodes 56a-56h and the conductive fluid (positioned beneath the curable fluid 12 in FIG. 6). The electrodes 56a-56h may form individual active areas of the interior surface 22. The different voltages may allow the interior surface 22 of the fluid chamber 52 to have a different wettability at corresponding portions of the interior surface 22 of the fluid chamber 52. For example, the electrodes 56c and 56g may have a greater voltage between these electrodes (56c, 56g) and the conductive fluid than the voltage between the electrodes 56a and 56e and the conductive fluid. The portions of the interior surface 22 of the fluid chamber 52 at the electrodes 56c and 56g may accordingly have a greater wettability than the portions of the interior surface 22 of the fluid chamber 52 at the electrodes 56a and 56e. The difference in wettability may result in an interface between the conductive fluid and the curable fluid 12 that is radially asymmetric. The contact angle of the conductive fluid 14 with the interior surface 22 of the side wall 16 may be different at different corresponding portions of the interior surface 22. A voltage difference between the conductive fluid and at least one of the multiple electrodes 56a-56h results in a variation in the shape of the surface of the curable fluid 12.

The radially asymmetric interface between the conductive fluid and the curable fluid 12 may allow for a greater variety of shapes of a lens or lens portion resulting from the curable fluid 12, including toric shapes which may provide cylinder power for ophthalmic lenses. Aspheric shapes may also result. In the embodiment shown in FIG. 6, the electrodes 56a-56h combine to form a cylinder electrode that is differently charged over the meridians of the electrodes (56a-56h).

The voltage of the electrodes 56a-56h may be varied as desired to result in a lens or lens portion having desired optical properties. The control of the electrode (56a-56h) voltage may occur through a variety of methods. Such methods may include amplitude modulation and/or phase and/or time delays, which may control the electrical excitation of individual electrodes to enable a better end-surface shape control or to generate lens surfaces with a higher relative degree of complexity, such as (high order) aspheres, and tori. Methods may include varied electrical amplitude pulses in time and space to the various electrodes (56a-56h).

In one embodiment, additional electrode(s), such as the additional electrode shown in regard to FIG. 4 may be utilized, such that they are positioned interior of the fluid chamber cavity. The electrode(s) may be positioned within the fluid chamber cavity, and may operate in combination with a respective electrode 56a-56h, to produce a desired shape of the interface between the conductive and curable fluids.

Although the fluid chamber 52 is shown to include eight electrodes 56a-56h in spaced position around the curable fluid 12 (e.g., a diced ring array), in other embodiments the number and position of the electrodes may be varied as desired. In one embodiment, a single electrode variably charged may be used to vary a shape of the interface between the conductive fluid and the curable fluid 12. In one embodiment, the shape of the interior surface 22 of the fluid chamber 52 may have a shape such as a rectangular, elliptical, or other shape, as discussed in regard to the fluid chamber 10 of FIG. 1. In one embodiment, the interior surface 22 of the fluid chamber 52 may be angled to result in a lens or portion of a lens having angled side portions.

In one embodiment, a controller 36 as shown in FIG. 7 may be used to control the voltage between the conductive fluid and the electrode 56a-56h in a desired manner, and accordingly may control the shape of the interface between the conductive and curable fluids.

FIG. 7 illustrates a side view of an embodiment of a fluid chamber 58 positioned upon a portion of an intraocular lens. The portion of the intraocular lens in FIG. 7 comprises a base intraocular lens 60 including an optic portion 62 and haptics 64 extending outward from the optic portion 62. The optic portion 62 is the portion of the intraocular lens 60 that light passes through to provide an image on the patient's retina. The haptics 64 extend from the optic portion 62 to hold the intraocular lens 60 in the patient's eye. In other embodiments, the haptics 64 may be excluded from the intraocular lens 60.

The fluid chamber 58 may be positioned on the anterior surface 66 of the base intraocular lens 60. In other embodiments, the fluid chamber 58 may be positioned on the posterior surface 68 of the base intraocular lens 60.

The fluid chamber 58 may be configured with an open end, which in FIG. 7 is in contact with the base intraocular lens 60. The other end of the fluid chamber 58 may include an end wall 70 that seals the cavity 72 of the fluid chamber 58. In other embodiments, the end wall 70 may be excluded and this end of the fluid chamber 58 may be open. In one embodiment, the end wall 70 may be made of a flexible membrane to allow shrinkage of the curable fluid 74 during curing. In one embodiment, a reservoir of conductive fluid may be provided to allow the curable fluid 74 to shrink without the introduction of tension stress in the material due to the creation of an under pressure in the fluid chamber 58. It is preferred that tension stresses are avoided as they can result in stress deformation and/or shrink marks in the resulting lens or portion of a lens.

The curable fluid 74 is in contact with the base intraocular lens 60. In FIG. 7, the curable fluid 74 is in contact with the anterior surface 66 of the base intraocular lens 60. In other embodiments, the curable fluid 74 may be in contact with the posterior surface 68 of the base intraocular lens 60, or other portions of the base intraocular lens 60, including the entirety of the base intraocular lens 60. Preferably, the curable fluid 74 is in contact with a portion of the base intraocular lens 60 that is within the optical zone of the base intraocular lens 60. The optical zone is the area of the base intraocular lens 60 that light passes through to provide an image on the patient's retina. The curable fluid 74 may be made of the same material described in regard to the curable fluid 12 of FIG. 1.

The conductive fluid 76 is in contact with the curable fluid 74 at an interface 78, similar to the contact between the conductive fluid 14 and the curable fluid 12 described in regard to FIG. 1. The conductive fluid 76 has a surface 80 that faces the curable fluid 74 at the interface 78, and the curable fluid 74 has a surface 82 that faces the conductive fluid 76 at the interface 78. The conductive fluid 76 may be made of the same material described in regard to the conductive fluid 14 of FIG. 1.

The curable fluid 74 may be configured to have a greater density than the conductive fluid 76, such that the conductive fluid 76 floats upon the curable fluid 74 and the curable fluid 74 is positioned on the base intraocular lens 60 positioned beneath the curable fluid 74. In one embodiment, the fluid chamber 58 and base intraocular lens 60 may be kept upside down, such that the conductive fluid 76 floats on top of the curable fluid 74 and is located between the base intraocular lens 60 and the curable fluid 74. This may prevent the curable fluid 74 from contacting the base intraocular lens 60 and from being partially dissolved in the material of the base intraocular lens 60. Prior (or just before) the curing of the curable fluid 74, the fluid chamber 58 and base intraocular lens 60 may be rotated into the position in which the curable fluid 74 contacts the base intraocular lens 60. In another embodiment, the conductive fluid 76 may have a greater density than the curable fluid 74. In such an embodiment, the base intraocular lens 60 may be held right side up, and then rotated upside down to allow the curable fluid 74 to contact the base intraocular lens 60 prior to curing.

The side wall 84 may be configured similarly as the side wall 16 described in regard to FIG. 1. The side wall 84 may include an electrode 86 that is configured similarly as the electrode 24 described in regard to FIG. 1. The side wall 84 may include an insulator layer 88 that is configured similarly as the insulator layer 26 described in regard to FIG. 1. The insulator layer 88 may be made out of a hydrophobic material or include a hydrophobic coating, in a similar manner as the insulator layer 26 described in regard to FIG. 1.

The electrode 86 may be configured to vary the shape of the interface 78 by varying a voltage between the electrode 86 and the conductive fluid 76, in a similar manner as described in regard to the electrode(s) described in regard to FIGS. 1-6. The electrode 86 may be configured to control the shape of interface 78 by varying the wettability of the surface 90 of the side wall 84. The variation in the shape of the interface 78 may provide a desired lens surface shape for the surface 82 of the curable fluid 74 when the curable fluid 74 is cured. The contact angle of the conductive fluid 76 with the interior surface 90 of the side wall 84 may be varied as desired.

In the embodiment of FIG. 7, a controller 36 may be used to control the voltage of the electrode 86. The controller 36 may be configured to allow a user to set a desired shape for the interface 78. The controller 36 may control the voltage of the electrode 86 to result in the desired geometry of the interface 78. The controller 36 may produce a lens surface for the curable fluid 74 that has the desired shape. In one embodiment, the controller 36 may be configured for a user to input desired optical properties of the resulting lens surface of the curable fluid 74. The optical properties such as lens power, cylinder power, add power, asphericity, and other optical properties may be input into the controller 36, and the controller 36 may vary the voltage of the electrode 86 to produce a lens surface having these properties. Shapes of the interface 78 and resulting lens surface may be concave, convex, planar, toric, or aspheric, or other shapes as desired.

The controller 36 may include a processor to perform the functions of the controller 36. The processor may be configured to control the electrode 86 and perform other functions of the controller 36. The controller 36 may also include a memory. The memory may store a listing of the desired optical properties of the lens surface in a database, and may store a correspondence between the desired optical properties and the voltage of the electrode 86 in the database. For example, the memory may store the correct voltage for the electrode 86 to result in a lens surface having a negative spherical power of a certain amount. Multiple optical properties of the lens surface, discussed throughout this application may be stored in the memory, as well as the correspondence between these optical properties and the voltage of the electrode 86. A user may select a desired optical property and the controller 36 may be configured to automatically produce a lens surface having the desired optical property, through control of the voltage of the electrode 86 or through other methods disclosed in this application.

In one embodiment, the controller 36 may include a feedback system, to allow feedback on the optical properties of the lens surface that result from the voltage of the electrode 86. The feedback system may allow the controller 36 to determine whether the voltage of the electrode 86 is resulting in the desired lens surface, and may allow the controller 36 to produce corrections to produce the desired properties of the lens surface. The feedback system may include a sensor 94 discussed in this application.

In one embodiment, the controller 36 may be configured to account for post-curing shrinkage of the curable fluid 74 in order to produce the desired lens surface.

In one embodiment, the controller 36 may be configured to account for the material of the curable fluid 74, to produce a desired lens surface. The memory may be configured to include a database that stores a listing of the possible materials of the curable fluid 74 and a correspondence between the desired optical properties of the lens, the material of the curable fluid, and the voltage of the electrode 86. A user may select a desired optical property and a material of the curable fluid 74, and the controller 36 may be configured to automatically produce a lens surface having the desired optical property based on the material of the curable fluid 74 and the desired optical properties of the lens. The controller 36 may produce the lens surface through control of the voltage of the electrode 86 or through other methods disclosed in this application.

The curable fluid 74 is partially or fully cured when positioned on the intraocular lens base 60. The curing of the curable fluid 74 may bond the curable fluid 74 to the intraocular lens base 60 and accordingly form a lens for the intraocular lens base 60. The bonding of the curable fluid 74 may result from absorption of the curable fluid 74 by the anterior surface 66, to create an interpenetrating network. The bonding may result from other forms of bonding as desired. Upon the curable fluid 74 being partially or fully cured, the fluid chamber 58 and the conductive fluid 76 may be removed from the base intraocular lens 60. The curing process may include photo curing or thermal curing, or a combination thereof, as disclosed in this application.

In an embodiment in which the curing process includes photo curing, the light for curing the fluid 74 may pass through the end wall 70. In other embodiments, the light may pass through the side wall 84, or through the base intraocular lens 62. Any portion of the end wall 70, side wall 84, and/or base intraocular lens 60 may be optically transparent to allow light to pass therethrough. A light source 92 may be used to at least partially cure or fully cure the curable fluid 74. The light source 92 may comprise a lamp, a light emitting diode, an excimer, a laser, or other form of light source, or multiples or combinations thereof. The light source 92 may be configured to produce light that passes through the end wall 70, or the side wall 84, or the base intraocular lens 62 as desired. In one embodiment, the operation of the light source 92 may be controlled with the controller 36, to produce the methods disclosed in this application.

In an embodiment in which the curing process includes thermal curing, a thermal control device, such as a heater or cooler, or combination thereof, may be used to vary the temperature of the curable fluid 74. The thermal control device may be used in combination with the light source 92 in an embodiment in which both photo and thermal curing is utilized.

The curable fluid 74 may produce a lens on the base intraocular lens 60. The lens resulting from the curable fluid 74 may comprise the only lens on the base intraocular lens 60, or may operate in combination with another lens. For example, the opposing surface of the base intraocular lens 60 (shown in FIG. 7 as posterior surface 68) may include a lens surface, and the lens resulting from the curable fluid 74 may operate in combination with this lens surface. In other embodiments, the lens resulting from the curable fluid 74 may overlay and form upon a lens surface of the intraocular lens 60, and may modify the optical properties of this surface.

In other embodiments, a fluid chamber may be positioned on both the posterior surface 68 and the anterior surface 66 of the base intraocular lens 60. A lens surface may be formed on both surfaces 66, 68 according to the methods disclosed in this disclosure. In one embodiment, the lens surface formed on a surface of the base intraocular lens may be used to provide corrections for any deficiencies in the lens surface that is formed on the opposite surface of the base intraocular lens, such as any unwanted post-curing shrinkage or failure of the lens surface to properly cure (e.g., due to blockage of the curing light due to UV chromophores in the base intraocular lens).

The form of the intraocular lens 60 may vary from the form shown in FIG. 7. In other embodiments, the opposing surface of the base intraocular lens 60 (shown in FIG. 7 as posterior surface 68), or the surface of the base intraocular lens 60 that the curable fluid 74 is formed upon (shown in FIG. 7 as posterior surface 68), may have planar, concave, convex, or other shapes as desired. Either surface of the intraocular lens may comprise an optical surface such as a diffractive pattern, or optical zones, or other form of optical surface. In other embodiments, the haptics 64 may be excluded or the configuration of the haptics 64 may be varied as desired. Various types of base intraocular lenses may be utilized, including base intraocular lenses with haptics, without haptics, with haptics constructed into the material of the intraocular lens, and haptics not constructed into the material of the intraocular lens, among others. In other embodiments, other features of an intraocular lens may be utilized in the resulting intraocular lens, including a posterior capsule opacification (PCO) edge or other desired features.

Figure 8:
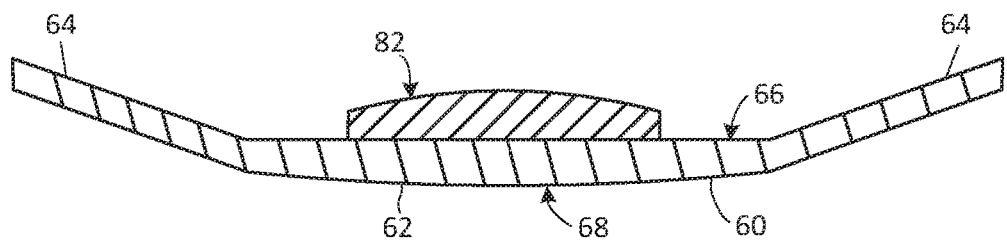
FIG. 8 illustrates a side cross sectional view of an intraocular lens produced from the fluid chamber and intraocular lens base shown in FIG. 7.

Upon the curable fluid 74 being bonded to the base intraocular lens 60, the resulting intraocular lens may be cleaned, polished, coated, further shaped, or may have other finishing processes applied to the resulting intraocular lens. FIG. 8 illustrates an intraocular lens formed from the bonding of the curable fluid 74 to the base intraocular lens 60. The fluid chamber 58 and the conductive fluid 76 have been removed from the base intraocular lens 60. The lens surface 82 corresponds to the surface 82 of the curable fluid 74 in FIG. 7. The resulting intraocular lens may comprise an accommodating intraocular lens for providing accommodating movement in the eye, or a monofocal or multifocal intraocular lens, or other form of intraocular lens. In one embodiment, a variety of process parameters for producing a desired lens surface may be input into the controller 36. The process parameters may include electrode voltage, curing light intensity profile (in an embodiment in which photo curing is utilized), curing temperature profile (in an embodiment in which thermal curing is utilized), curing time, and post curing time. The controller 36 may be configured to execute the parameters to produce the desired lens surface result. In one embodiment, the memory of the controller 36 may include a database that includes the process parameters for a desired intraocular lens. The processor of the controller 36 may be configured to retrieve and execute the process parameters upon request, to produce the desired intraocular lens.

In one embodiment, a method of producing the lens surface may include inputting process parameters for producing a desired lens surface, which may include electrode voltage, curing light intensity profile (in an embodiment in which photo curing is utilized), curing temperature profile (in an embodiment in which thermal curing is utilized), curing time, and post curing time. The electrode voltage may be applied to produce the desired electrowetting effect. While the electrowetting effect is occurring, curing may occur through the curing light intensity profile and/or curing temperature profile being applied in a curing process. A feedback system, such as a sensor 94 as disclosed in this application or other form of feedback device, may be used to measure the optical properties of the lens surface and determine whether the desired optical properties of the lens surface results. The feedback system may include a wavefront sensor to determine whether the desired optical properties of the lens surface are being met, including the desired lens power, cylinder power, asphericity, and the like.

A repetitive control cycle may occur of measuring the actual optical properties of the lens surface and comparing it to the desired optical properties of the lens surface. The process parameters may be modified during the lens formation process to result in the desired optical properties of the lens surface. When the curing process concludes, the final optical properties of the lens surface may be measured by a sensor 94 or the like. The process parameters used during the lens formation process, the in-process optical properties of the lens, and the final optical properties of the lens may be stored in a database to refine the initial process parameter values. The refinement process may include a periodic multi variate analysis of the data or other processing of the data. Other forms of self learning routines may be utilized as desired. In one embodiment, the processes may be performed by the controller 36, and the process parameters used during the lens formation process, the in-process optical properties of the lens, and the final optical properties of the lens may be stored in a database of the controller's 36 memory. In one embodiment, the desired optical properties of the lens may be input into the controller 36, and the controller 36 may be configured to retrieve the corresponding process parameters stored in its memory and produce the desired lens surface.

In one embodiment, a plurality of electrodes may be utilized to shape the interface 78 as desired, in a similar manner as discussed in regard to the electrodes of FIG. 6.

In one embodiment, additional electrode(s), such as the additional electrode shown in regard to FIG. 4 may be utilized, such that the electrode(s) are positioned interior of the fluid chamber cavity. The electrode(s) may be positioned adjacent to the wall 70 to produce a desired shape of the interface 78.

The methods described herein may comprise manufacturing methods that produce an ophthalmic lens, which may comprise an intraocular lens, a contact lens, an eyeglass lens, or other form of ophthalmic lens. The methods may be performed at a manufacturing facility or may be performed locally with an optical practitioner such as an optometrist, ophthalmologist, or optician. The optical practitioner may be able to perform an assessment of the desired properties of a lens for a patient and determine the desired optical properties and structural properties of a lens for a patient. The optical practitioner may be able to produce a custom lens for the patient locally, which may include a desktop manufacture of the lens. This feature may beneficially allow an optical practitioner to readily produce a lens that meets the needs of a patient, and may reduce the number of lenses the practitioner keeps on stock or in consignment. Methods discussed in this application may be performed locally with an optical practitioner, unless stated otherwise.

The apparatuses discussed herein may be used to perform the methods discussed in this application. The apparatuses discussed herein may comprise a system used to produce a desired lens. In an embodiment in which the method is performed locally with an optical practitioner, the optical practitioner may locally utilize the apparatuses, including the fluid chambers, fluids, controllers, light sources, and feedback systems (including sensors) discussed in this application. The fluid chambers may be filled with the fluids (conductive and/or curable) by the optical practitioner. In one embodiment, the fluid chambers may come pre-filled to the practitioner as cartridges or the like. In one embodiment, the fluid chambers may come to the practitioner affixed to a corresponding intraocular lens base. In other embodiments, the practitioner may affix the fluid chamber to a desired intraocular lens base.

Figure 9:
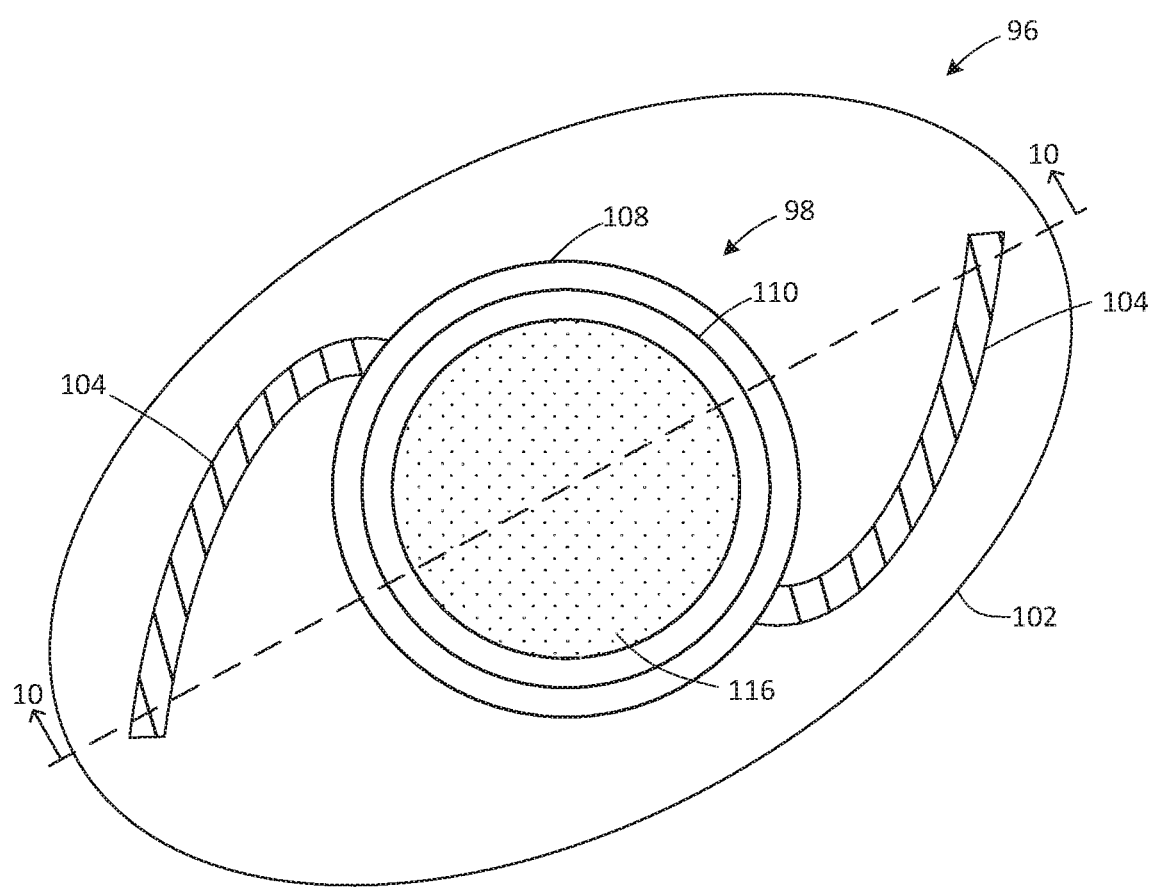
FIG. 9 illustrates a top view of a cartridge according to an embodiment of the present disclosure.
Figure 10:
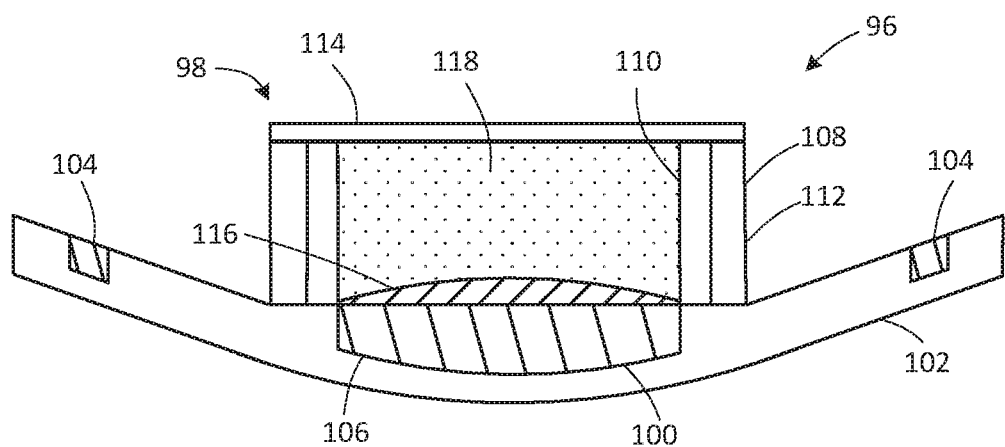
FIG. 10 illustrates a side cross section view along line 10-10 of FIG. 9.

FIGS. 9 and 10 illustrate an embodiment in which a cartridge 96 includes a fluid chamber 98 and a base intraocular lens 100. FIG. 9 illustrates a top view of the cartridge 96 and FIG. 10 illustrates a side cross sectional view of the cartridge 96 along line 10-10. The cartridge 96 may be configured to be used by an optical practitioner in forming an intraocular lens.

The cartridge 96 may include a bottom housing 102, which may be a mold for a base intraocular lens 100. The base intraocular lens 100 may be secured to the bottom housing 102 such that the base intraocular lens 100 is held in position during the lens formation process. The base intraocular lens 100 may be secured to the bottom housing 102 with a friction fit or the like, or in one embodiment the base intraocular lens 100 may have been molded into the bottom housing 102 and remains in the bottom housing 102. The base intraocular lens 100 may include haptics 104 that extend outward from the optic portion 106 of the base intraocular lens 100. The haptics 104 may have a spiral configuration extending along the bottom housing 102. In other embodiments, the shape and configuration of the haptics 104 may be varied. In other embodiments, the haptics 104 may be excluded.

The fluid chamber 98 may be configured similarly as the fluid chamber 58 discussed in regard to FIG. 7. The fluid chamber 98 may include a sidewall 108 that includes an insulator layer 110 and an electrode 112, as discussed in regard to the embodiment of FIG. 7. In one embodiment, the insulator layer 110 may be excluded. In one embodiment, the electrode 112 may not be a portion of the sidewall 108. The electrode 112 may be part of an electrowetting and curing device that the cartridge 96 is used in combination with, or inserted into, to produce the intraocular lens. In one embodiment, the fluid chamber 98 may be held in a top housing, which may be a top mold, to secure the fluid chamber 98 to the bottom housing 102.

In one embodiment, a plurality of electrodes may be utilized to shape the interface between the curable fluid 116 and conductive fluid 118 as desired, in a similar manner as discussed in regard to FIG. 6.

In one embodiment, additional electrode(s), such as the additional electrode shown in regard to FIG. 4 may be utilized, such that the electrode(s) are positioned interior of the fluid chamber cavity. The electrode(s) may be positioned adjacent to the wall 114 to produce a desired shape of the interface between the curable fluid 116 and conductive fluid 118.

An end wall 114 may seal the fluid chamber 110. The end wall 114 may be configured similarly as the end wall 70 referred to in FIG. 7. In one embodiment, the end wall 114 may be optically transparent and may be flexible to account for shrinkage of the curable fluid 116.

In one embodiment, the fluid chamber 110 may not come pre-filled. The fluid chamber 110 may be filled by an optical practitioner.

The cartridge 96 may be selected to result in an intraocular lens having desired properties. The properties may include optical properties or structural properties of the intraocular lens, which may include the design of the intraocular lens, the material of the intraocular lens, among other properties. The curable fluid 116 may be shaped and cured in a manner discussed in this application.

In one embodiment, the cartridge 96 may be held upside down from the configuration shown in FIG. 10, such that the curable fluid 116 does not contact the base intraocular lens 100. Keeping the curable fluid 116 out of contact with the base intraocular lens 100 may reduce the possibility of swelling of the material of the base intraocular lens 100. Prior to shaping and curing, the cartridge 96 may be rotated to contact the base intraocular lens 100.

Upon the curable fluid 116 being processed to the desired amount on the base intraocular lens 100, the fluid chamber 98 and conductive fluid 118 may be removed. If the fluid chamber 98 is held in a top housing, the top housing may be removed as well. The base intraocular lens 100 may be removed from the bottom housing 102 prior to implantation. The top housing and bottom housing 102 may be discarded, with both serving as a disposable portion of the cartridge 96.

Figure 11:
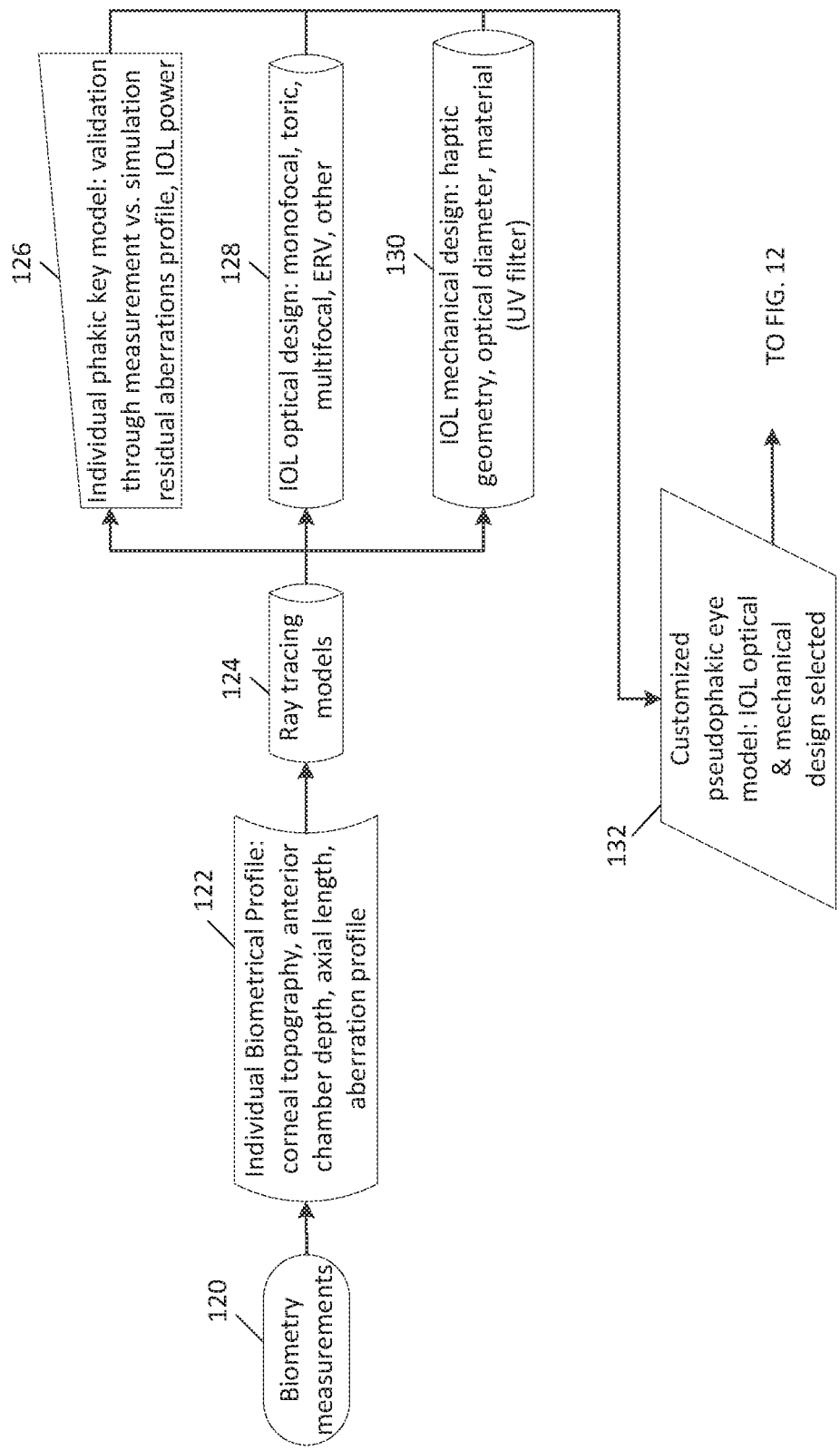
FIG. 11 illustrates a method according to an embodiment of the present disclosure.
Figure 12:
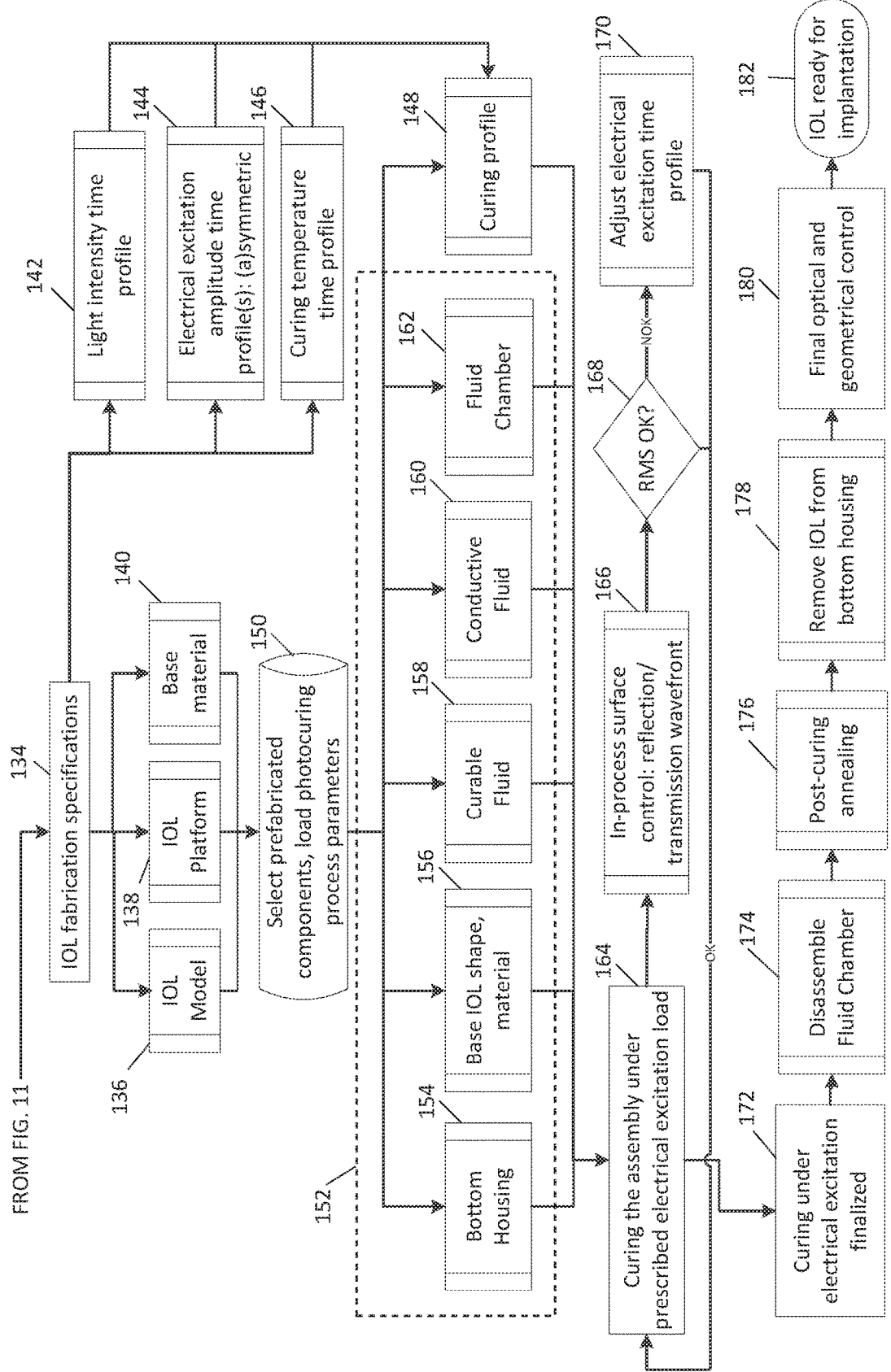
FIG. 12 illustrates a method according to an embodiment of the present disclosure.

FIGS. 11 and 12 illustrate a method of producing an intraocular lens. The method may be performed by an optical practitioner, and may be used to produce a custom intraocular lens for a patient. The method may comprise a local desktop manufacture of a customized intraocular lens.

FIG. 11 illustrates a method of performing an assessment of the desired properties of an intraocular lens for a patient. The properties may include optical and structural properties of the intraocular lens. The method may result in a personalized visual outcome for a patient.

In step 120, the biometry of a patient may be measured. The characteristics of the patient's eye may be measured through a variety of methods and devices including optical measurement, ultrasound measurements, or a combination of both. In other embodiments, other methods or devices may be used to measure the biometry of a patient's eye. The biometry measurements will be used to determine the desired properties of an intraocular lens to be created for the patient.

The biometry measurements may include a measurement of the corneal topography, anterior chamber depth, axial length, and aberrations profile, of the eye. Other characteristics of the eye may be retrieved as desired. The biometry measurements may be taken and recoded for both eyes of the patient if an intraocular lens is desired for each eye.

In step 122, the biometry measurements of the patient may be stored to create an individual biometrical profile for the patient. The profile may include the biometric measurements of the eye including corneal topography, anterior chamber depth, axial length, and aberrations profile, and other characteristics of the eye as desired.

In step 124, the biometrical profile of the patient may be used in a model to determine desired properties of an intraocular lens used for optical correction. The model used may be a ray tracing model. In other embodiments, other models or methods may be utilized to determine properties of an intraocular lens.

The model may be used to determine properties of the intraocular lens including optical properties and structural properties of the intraocular lens.

In step 126, the model may result in a model of preferred vision of a phakic eye. This model may be used to determine the desired properties of the intraocular lens including the lens power, cylinder power, add power, asphericity, or any desired higher order aberrations, among others. The desired model may be matched against other intraocular lenses used for eyes with similar characteristics. The desired model may be used in a simulation of a residual aberrations profile.

In step 128, the model may result in a determination of intraocular lens optical design, including whether the intraocular lens will be monofocal, toric, multifocal, have an extended range of vision (ERV), among others.

In step 130, the model may result in a determination of intraocular lens mechanical design, including the haptic geometry, the optical diameter, the material, including whether UV filter will be used, among others.

The steps 126, 128, 130 may result in a customized pseudophakic eye model 132. The eye model may include the properties of the intraocular lens to be produced, including the optical properties and structural properties determined in steps 126, 128, and 130.

FIG. 12 illustrates a method for custom fabrication of the intraocular lens.

In step 134, fabrication specifications of the desired intraocular lens may be provided. The fabrication specifications are based on the desired properties of the intraocular lens determined from the eye model in step 132. The fabrication specifications may be determined in a processor, or may be matched with pre-stored specifications in a memory for a particular eye model.

The fabrication specifications in step 136 may include the intraocular lens model, which includes the optical properties determined for the desired intraocular lens.

The fabrication specifications in step 138 may include the intraocular lens platform, which is the intraocular lens design to be used, such as monofocal, multifocal, ERV, or others.

The fabrication specifications in step 140 may include the base material, which is the material that the base intraocular lens is made from.

The fabrication specifications in step 142 may include a light intensity profile, in an embodiment in which photocuring is utilized. The light intensity profile may be a light intensity time profile. The light intensity profile may be the light intensity and manner of light application for the curable fluid to cure the curable fluid in a desired manner.

The fabrication specifications in step 144 may include an electrical excitation profile for the electrode(s) used in the electrowetting process. The electrical excitation profile may be a time profile, and may be an excitation amplitude profile. In one embodiment, the profile may be configured to produce a symmetric or asymmetric lens surface resulting from the curable fluid. The electrical excitation profile may be the manner of electrical excitation to produce the desired lens surface shape for the intraocular lens.

The fabrication specifications in step 146 may include a curing temperature profile, in an embodiment in which thermo curing is utilized. The thermo curing may be used in combination with the photo curing. The curing temperature profile may be a time profile. The curing temperature profile may be the curing temperature and manner of thermal application for the curable fluid to cure the curable fluid in a desired manner.

The fabrication specifications of steps 142, 144, and 146 may result in a curing profile 148 to be used in a manufacture of an intraocular lens. The curing profile 148 may be a photo curing profile in an embodiment in which photo curing is utilized.

The fabrication specifications of steps 136, 138, and 140 may be used in step 150 to select components for use in the formation of the intraocular lens. The process parameters resulting from the curing profile 148 may also be loaded.

The selection of the components may in step 152 be either a selection of a preassembled cartridge (which may be a cartridge discussed in this application), or may involve a combination of components. In an embodiment in which a preassembled cartridge is utilized, the cartridge may be selected based on the desired components from steps 136, 138, and 140. In an embodiment in which components are assembled, selection of components similarly may be based on desired components from steps 136, 138, and 140.

The components may include a bottom housing 154, which may be a bottom mold. The bottom housing may hold all or a portion of the base intraocular lens and any associated haptics.

The components may include a base intraocular lens 156. The shape and material of the base intraocular lens may be selected as desired. The base intraocular lens may be positioned in the bottom housing of step 154, or may come pre-positioned in the bottom housing in an embodiment in which a cartridge is used.

The components may include a curable fluid 158. The curable fluid 158 may include a monomer or may include other forms of curable fluids discussed in this application.

The components may include a conductive fluid 160. The conductive fluid may comprise an electrolyte, or other form of conductive fluid discussed in this application.

The components may include a fluid chamber 162. The fluid chamber 162 may include one or more electrodes as discussed in this application. The fluid chamber 162 may be provided in a top housing, which may be a top mold. In an embodiment in which a cartridge is used, the fluid chamber may already include the curable fluid and the conductive fluid, and may be coupled to the remainder of the cartridge. The fluid chamber may be held in a position (such as upside down) so that the curable fluid does not contact the base intraocular lens until a time for electrowetting and curing. In an embodiment in which the components are assembled on site, the fluid chamber may be filled with the curable fluid and the conductive fluid.

The components for electrowetting and curing 152 and the curing profile 148 may be used in a curing process under electrical excitation caused by electrowetting 164. In an embodiment in which a cartridge is utilized, the cartridge may be taken out of its packaging and may be rotated such that the curable fluid contacts the base intraocular lens. The cartridge may be used, or inserted into, an electrowetting and curing apparatus, which may be a curing chamber.

The curing profile 148 may be used to determine the electrical excitation to be applied to the fluids in the fluid chamber to provide the desired electrowetting effect and shape of the optical surface. A curing process, either via photo curing, or thermal curing, may be utilized.

In step 166, a feedback system may be used to determine if the optics of the lens being formed by the electrowetting and curing process is resulting in the desired optical properties. In one embodiment, an optical wavefront testing method may be used to determine if the desired optical properties are being met. This may be a reflection or transmission wavefront testing method.

In step 168, a check may occur to see if the optics of the lens being formed by the electrowetting and curing process is resulting in the desired optical properties in step 166. The check may be a root mean square check. If the check if met, any additional electrowetting and curing processing may occur 164 until the curing process is finalized in step 172. If the check is not met, then the electrowetting and curing process may be adjusted accordingly 170, using any method disclosed in this application. The method may include adjusting the electrical excitation profile of the electrode(s) of the fluid chamber, or adjusting the curing process. The electrowetting and curing processing may occur 164 until the check is met 168, and then the curing process is finalized in step 172.

Upon the curing process being finalized in step 172, the fluid chamber and conductive fluid may be removed in step 174. If the fluid chamber and conductive fluid are held in a top housing such as a top mold, then the top mold may be removed.

In step 176, a finishing process of post-curing annealing may be applied to the intraocular lens.

In step 178, the intraocular lens may be removed from a bottom housing such as a bottom mold if one is utilized.

In step 180, finishing processes may be applied to the intraocular lens, including final optical and geometrical control. Other finishing processes may be applied as desired.

In step 182, the intraocular lens is complete and is ready for implantation.

The steps of FIGS. 11 and 12 may be excluded or modified as desired. Additional steps may be included if desired.

All or a portion of the steps of FIGS. 11 and 12 may be performed on site by an optical practitioner, such as a surgeon. In one embodiment, portions of the method may be completed off-site.

The steps of FIGS. 11 and 12 may be operated by a controller as desired, such as the controller 36 discussed in regard to FIG. 7. The processor of the controller 36 may operate the steps. The eye models and fabrication specifications, as well as the processes for lens fabrication, may be stored in a memory of the controller 36.

In one embodiment, a repetitive control cycle discussed in this application may be used to optimize the electrowetting and curing process.

The steps of FIGS. 11 and 12 may be performed for one or both eyes of a patient.

In one embodiment, the steps of FIGS. 11 and 12 may be used to produce another form of lens, including a contact lens or eyeglass lens.

Figure 13:
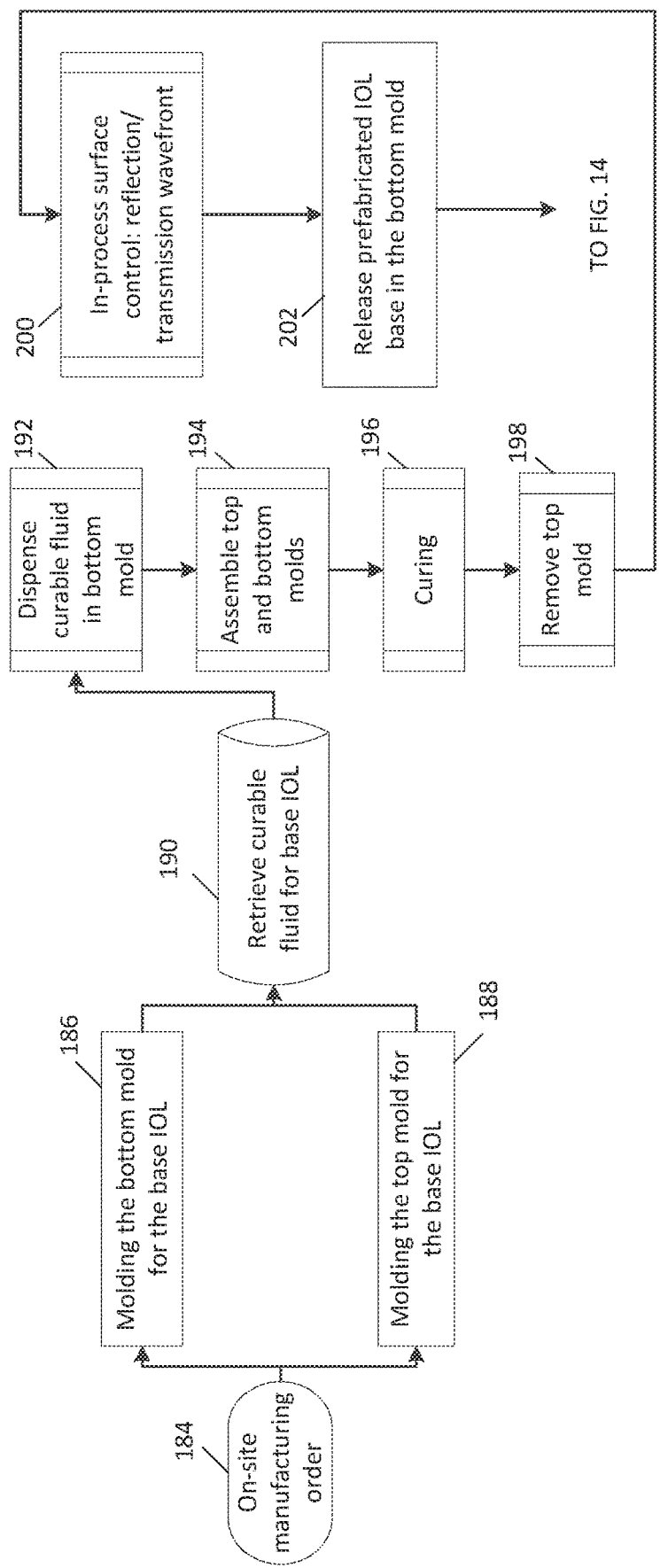
FIG. 13 illustrates a method according to an embodiment of the present disclosure.
Figure 14:
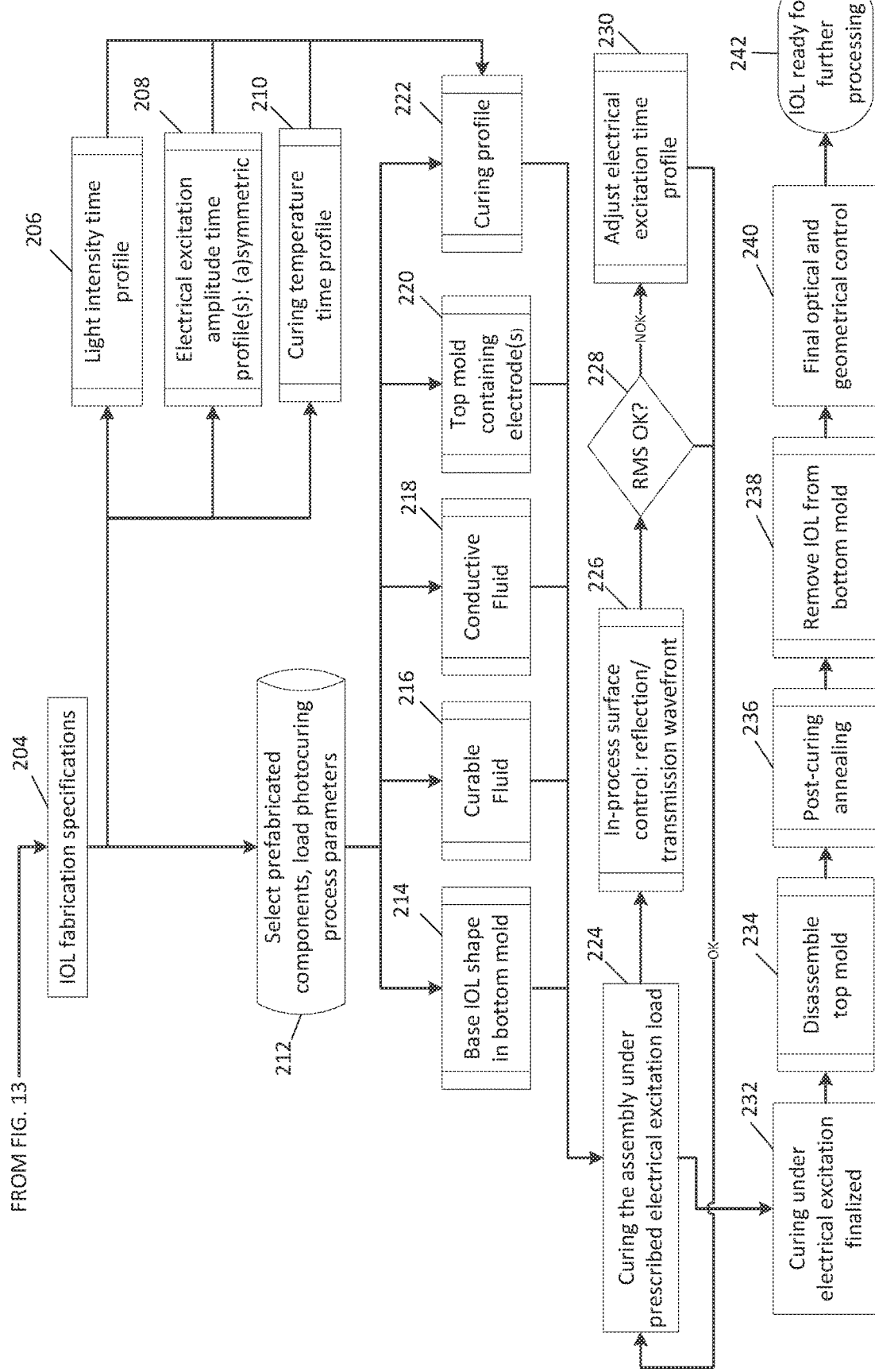
FIG. 14 illustrates a method according to an embodiment of the present disclosure.

FIGS. 13 and 14 illustrate a method for manufacture of an intraocular lens. The method of FIGS. 13 and 14 may be utilized in a high volume or factory manufacture of an intraocular lens.

FIG. 13 illustrates a method of fabrication of a base intraocular lens. In step 184, a manufacturing order may be provided. The manufacturing order may be received by the manufacturer. The manufacturing order may specify the properties of the intraocular lens to be produced, including optical properties and structural properties. The properties of the intraocular lens may include the properties of the base intraocular lens to be produced.

In steps 186 and 188, a mold is provided for the base intraocular lens. The mold is based on the desired properties of the base intraocular lens. The mold may be configured to include optical features desired for the base intraocular lens.

In step 186, the bottom mold for the base intraocular lens is provided. The bottom mold may be molded as desired.

In step 188, the top mold for the base intraocular lens is provided. The top mold may be molded as desired.

Either mold may include optical features of the base intraocular lens, if a surface of the intraocular lens will include an optical feature.

In step 190, the curable fluid is provided for the base intraocular lens. The curable fluid may be a monomer or other form of curable fluid. The type of curable fluid utilized would be based on the desired optical properties of the base intraocular lens.

In step 192, the curable fluid is dispensed into one of the molds, which may be the bottom mold.

In step 194, the top mold and the bottom mold are assembled.

In step 196, curing, such as photocuring or thermal curing, or a combination thereof, may be used to produce the base intraocular lens.

In step 198, a mold is removed, which may be the top mold.

In step 200, a determination of the optical properties of the base intraocular lens may be made to determine if the base intraocular lens has reached a desired state. An optical wavefront testing method may be used to determine if the desired optical properties have been acheived. The testing method may be a reflection or transmission wavefront testing method.

In step 202, a formed base intraocular lens is provided in the remaining mold, which may be the bottom mold. The base intraocular lens may be removed from the bottom mold if desired for later processing.

FIG. 14 illustrates a process for fabrication of an intraocular lens. In step 204, fabrication specifications may be provided to produce the intraocular lens. The fabrication specifications may be provided in the manufacturing order in step 184. In other embodiments, the fabrication specifications may be retrieved from a memory based on the desired properties of the intraocular lens or may be calculated to produce an intraocular lens that meets the manufacturing order in step 204.

The fabrication specifications in step 206 may include a light intensity profile, in an embodiment in which photocuring is utilized. The light intensity profile may be a light intensity time profile. The light intensity profile may be the light intensity and manner of light application for the curable fluid to cure the curable fluid in a desired manner.

The fabrication specifications in step 208 may include an electrical excitation profile for the electrode(s) used in the electrowetting process. The electrical excitation profile may be a time profile, and may be an excitation amplitude profile. In one embodiment, the profile may be configured to produce a symmetric or asymmetric lens surface resulting from the curable fluid. The electrical excitation profile may be the manner of electrical excitation to produce the desired lens surface shape for the intraocular lens.

The fabrication specifications in step 210 may include a curing temperature profile, in an embodiment in which thermo curing is utilized. The thermo curing may be used in combination with the photo curing. The curing temperature profile may be a time profile. The curing temperature profile may be the curing temperature and manner of thermal application for the curable fluid to cure the curable fluid in a desired manner.

The fabrication specifications of steps 206, 208, and 210 may result in a curing profile 222 to be used in a manufacture of an intraocular lens. The curing profile 222 may be a photo curing profile in an embodiment in which photo curing is utilized.

The fabrication specifications may be used in step 212 to select components for use in the formation of the intraocular lens. The process parameters resulting in the curing profile 222 may also be loaded.

The components may include the bottom housing 214 including the base intraocular lens. The bottom housing may be a bottom mold. The bottom mold 214 which may be provided from step 202. The bottom housing may hold all or a portion of the base intraocular lens and any associated haptics.

The components may include a curable fluid 216. The curable fluid 216 may include a monomer or may include other forms of curable fluids discussed in this application.

The components may include a conductive fluid 218. The conductive fluid may comprise an electrolyte, or other form of conductive fluid discussed in this application.

The components may include a fluid chamber 220. The fluid chamber 220 may include one or more electrodes as discussed in this application. The fluid chamber 220 may be provided in a top housing, which may be a top mold.

The components 214, 216, 218, 220 may be assembled for use in an electowetting and curing process.

The components for electrowetting and curing and the curing profile 222 may be used in a curing process under electrical excitation caused by electrowetting 224.

The curing profile 222 may be used to determine the electrical excitation to be applied to the fluids in the fluid chamber to provide the desired electrowetting effect and shape of the optical surface. A curing process, either via photo curing, or thermal curing, may be utilized.

In step 226, a feedback system may be used to determine if the optics of the lens being formed by the electrowetting and curing process is resulting in the desired optical properties. In one embodiment, an optical wavefront testing method may be used to determine if the desired optical properties are being met. This may be a reflection or transmission wavefront testing method.

In step 228, a check may occur to see if the optics of the lens being formed by the electrowetting and curing process is resulting in the desired optical properties in step 226. The check may be a root mean square check. If the check if met, any additional electrowetting and curing processing may occur 224 until the curing process is finalized in step 232. If the check is not met, then the electrowetting and curing process may be adjusted accordingly 230, using any method disclosed in this application. The method may include adjusting the electrical excitation profile of the electrode(s) of the fluid chamber, or adjusting the curing process. The electrowetting and curing processing may occur 224 until the check is met 228, and then the curing process is finalized in step 232.

Upon the curing process being finalized in step 232, the fluid chamber and conductive fluid may be removed in step 234. If the fluid chamber and conductive fluid are held in a top housing such as a top mold, then the top mold may be removed.

In step 236, a finishing process of post-curing annealing may be applied to the intraocular lens.

In step 238, the intraocular lens may be removed from the bottom housing such as a bottom mold.

In step 240, finishing processes may be applied to the intraocular lens, including final optical and geometrical control. Other finishing processes may be applied as desired.

In step 242, the intraocular lens is complete and is ready for further processing, including packaging.

The steps of FIGS. 13 and 14 may be excluded or modified as desired. Additional steps may be included if desired.

All or a portion of the steps may be aided by use of high volume manufacturing methods. The steps may be performed along a conveyor line of manufacturing, which may include curing tunnels. The components of the intraocular lens may be transported along a manufacturing system with steps being performed on the lens along the manufacturing line.

The steps of FIGS. 13 and 14 may be operated by a controller as desired, such as the controller 36 discussed in regard to FIG. 7. The processor of the controller 36 may operate the steps. The fabrication specifications, as well as the processes for lens fabrication, may be stored in a memory of the controller 36.

In one embodiment, a repetitive control cycle discussed in this application may be used to optimize the electrowetting and curing process.

In one embodiment, the processes may be used to provide an add-on lens (such as a 10th power increment, toric lens, or aspheric lens) to a lens on the base intraocular lens.

In one embodiment, the steps of FIGS. 13 and 14 may be used to produce another form of lens, including a contact lens or eyeglass lens.

Figure 15:
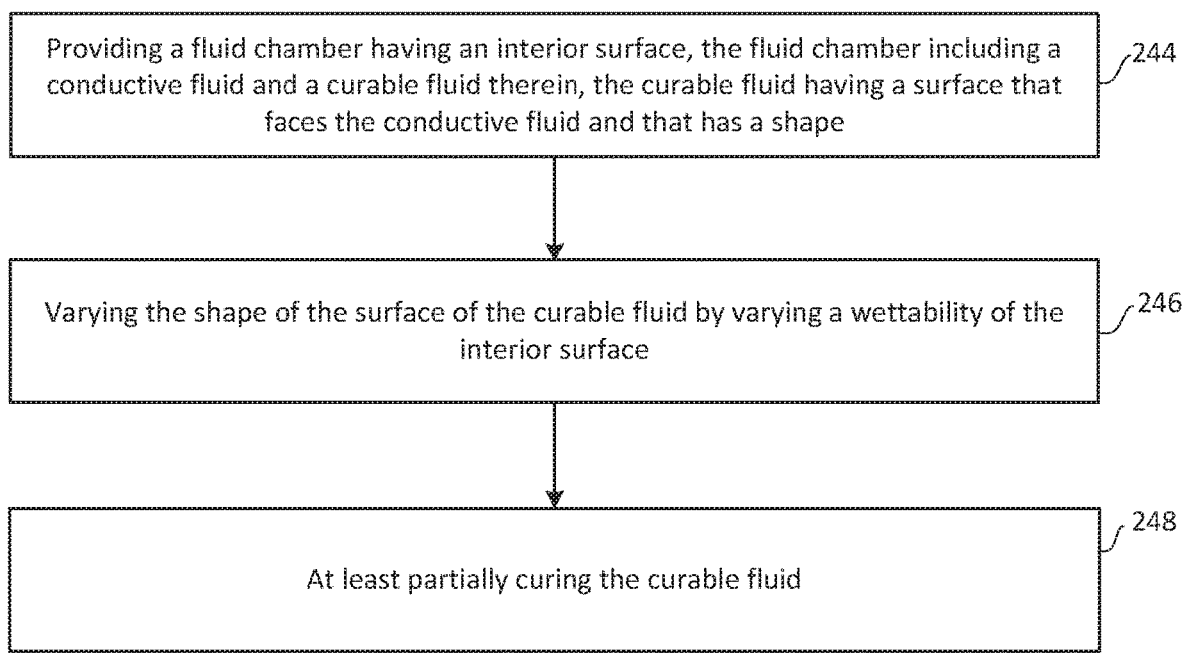
FIG. 15 illustrates a method according to an embodiment of the present disclosure.

FIG. 15 illustrates an embodiment of a method of this disclosure. In step 244 a fluid chamber is provided having an interior surface. The fluid chamber includes a conductive fluid and a curable fluid therein. The curable fluid has a surface that faces the conductive fluid and that has a shape. The step of providing the fluid chamber may be performed by using, having, or producing the fluid chamber.

Step 246 includes varying the shape of the surface of the curable fluid by varying a wettability of the interior surface.

Step 248 includes at least partially curing the curable fluid.

The apparatuses, systems, and methods of steps 244, 246, and 248 may be performed by the apparatuses, systems, and methods disclosed in this application. The method of FIG. 15 is not limited to the steps or description provided herein and may be modified by any of the apparatuses, systems, and methods disclosed in this application. In other embodiments, steps or portions of steps may be excluded.

Figure 16:
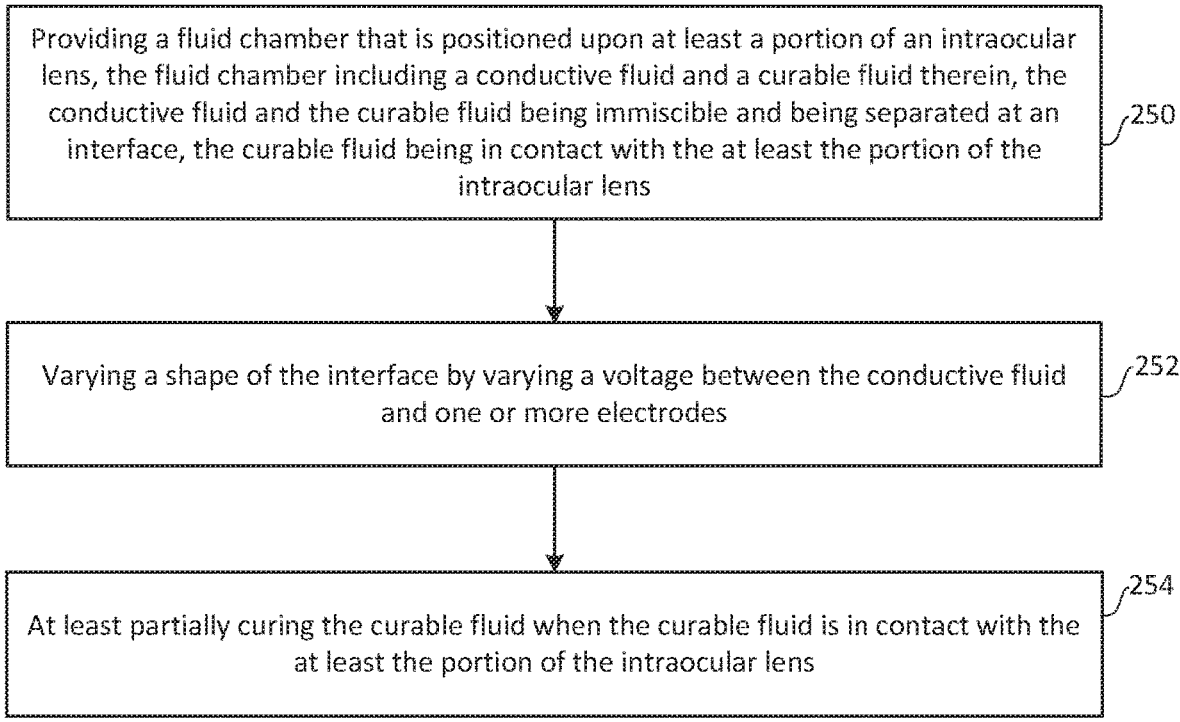
FIG. 16 illustrates a method according to an embodiment of the present disclosure.

FIG. 16 illustrates an embodiment of a method of this disclosure. In step 250 a fluid chamber is provided that is positioned upon at least a portion of an intraocular lens. The fluid chamber may include a conductive fluid and a curable fluid therein, the conductive fluid and the curable fluid being immiscible and being separated at an interface, the curable fluid being in contact with the at least the portion of the intraocular lens. The step of providing the fluid chamber may be performed by using, having, or producing the fluid chamber.

In step 250, as an example, the intraocular lens may include haptics and a lens surface on a posterior side of the intraocular lens. The anterior side of the intraocular lens may be planar or may have a base curvature to minimize the amount of curable fluid. A user may position the fluid chamber upon the anterior side of the intraocular lens. The user may fill the cavity of the fluid chamber with a specific quantity of curable fluid. The curable fluid may be made of the curable fluid material discussed in this application, including a monomer and may include a photo initiator. The conductive fluid may be filled on top of the curable fluid and the cavity of the fluid chamber may be closed. The conductive fluid may be made of the conductive fluid material discussed in this application, including an electrolytic fluid.

Step 252 includes varying a shape of the interface by varying a voltage between the conductive fluid and one or more electrodes.

In step 252, as an example, one or more of the electrodes may be charged to vary the shape of the interface. The shape of the interface may have a desired shape for a resulting lens surface and may be corrected for polymer post-curing shrinkage.

Step 254 includes at least partially curing the curable fluid when the curable fluid is in contact with the at least the portion of the intraocular lens.

In step 254, as an example, the curable fluid may be at least partially cured by being exposed to light (e.g., blue light). The anterior surface of the intraocular lens may be cured.

As an additional step, the fluid chamber and conductive fluid may be removed. The resulting intraocular lens may have finishing processes applied to it (e.g., cleaned). In other embodiments, a similar process may be used to produce a lens surface on the posterior surface of the intraocular lens, to provide shape corrections of the like.

The apparatuses, systems, and methods of steps 250, 252, and 254 may be performed by the apparatuses, systems, and methods disclosed in this application. The method of FIG. 16 is not limited to the steps or description provided herein and may be modified by any of the apparatuses, systems, and methods disclosed in this application. In other embodiments, steps or portions of steps may be excluded.

Additional apparatuses, systems, and methods of the present disclosure, which may be utilized in combination with any of the apparatuses, systems, and methods disclosed in this application, may include the following:

In one embodiment, the refractive index of the curable fluid discussed in this application (for example curable fluid 12 or 74) may be selected such that the refractive index of the resulting lens is different than a refractive index of an optic to which the resulting lens is affixed. For example, in the embodiment of FIG. 7, the refractive index of the curable fluid 74 may be different than the refractive index of the base intraocular lens 60 at the optical zone. This may result in a gradient refractive index across the intraocular lens. The gradient refractive index may serve to better mimic the architecture of a natural crystalline lens. A gradient refractive index may also serve to create an intraocular lens with a compensatory chromatic aberration level, which may assist in compensating for a chromatic aberration of the cornea. In one embodiment, layers of curable fluid made of different materials (with different refractive indexes) may be stacked upon each other to produce layers of material having different refractive indexes. A multi-layered lens optic may result. In addition, different curvatures of the layers may be produced. The multi-layered lens optic may result in enhanced peripheral vision for the patient.

In one embodiment, a light pattern may be applied to the curable fluid discussed in this application (for example curable fluid 12 or 74). The light pattern may be used in the curing process and may result in controlled shape variations for the curable fluid. For example, the light pattern may serve to cure the curable fluid in specified locations, which may vary the shape of the curable fluid at those locations. The curable fluid may polymerize at the locations, which will vary the local structure of the curable fluid. Controlled shape variations of the resulting lens may occur through this process. Once the controlled shape variations occur, the resulting lens may be fully cured by shining light upon the entirety of the lens. The controller 36 may operate the light source 92 or other elements of the manufacturing system to apply the light pattern. In one embodiment, the light pattern may be a predetermined light pattern. The predetermined light pattern may be stored in the memory of the controller 36 and produced by the light source 92, which may be under the control of the controller 36.

Figure 17:
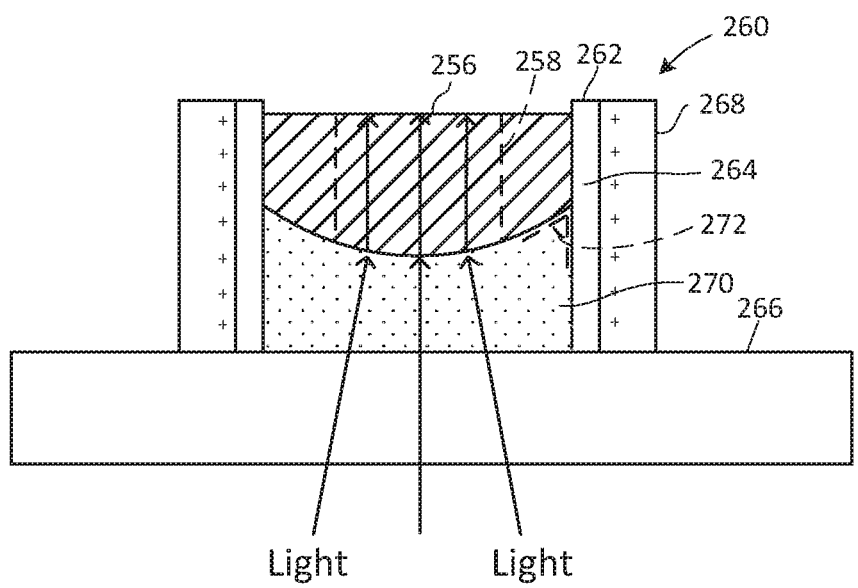
FIG. 17 illustrates a side cross sectional view of a fluid chamber according to an embodiment of the present disclosure.

In one embodiment, light may be applied to a portion of the curable fluid to initiate curing of the portion of the curable fluid. Before, during, or after the light is applied to the portion of the curable fluid, the electrowetting process (e.g., voltage of one or more electrodes) may be initiated or varied to produce a desired shape of the lens surface. FIG. 17, for example, illustrates an embodiment in which a portion of the curable fluid 256 is cured or partially cured with light. The portion of the curable fluid is indicated with reference number 258 in FIG. 17 between dashed lines. The fluid chamber 260 in FIG. 17 is configured similarly as the fluid chamber 10 discussed in regard to FIGS. 1-2. The fluid chamber may include an insulting layer 262 as part of a side wall 264, and may include an end wall 266. An electrode 268 or multiple electrodes may comprise part of the side wall 264. A conductive fluid 270 may be positioned in the fluid chamber 260. In other embodiments, the fluid chamber 260 may be configured as any fluid chamber disclosed in this application, including use with multiple electrodes (inside or outside of the cavity), electrodes separated from the side wall, multiple layers of conductive fluid, and/or use upon a base intraocular lens or as a cartridge, among other features.

In FIG. 17, light is radiated to cure or partially cure the portion 258 of the curable fluid 256. The lens surface shape of the portion 258 of the curable fluid 256 may be produced before or during the curing or partial curing process. For example, the electrowetting process may be used to set the contact angle 272 and the shape of the portion of the curable fluid 256. The voltage of the electrode 268 may be set to determine the shape of the portion of the curable fluid 256. In other embodiments, the electrowetting process may not yet occur, and the natural shape of the curable fluid 256 in contact with the conductive fluid 270 may be utilized. The light may be applied by a light source 94 (as shown in FIG. 7), and may be applied to the curable fluid in any direction as desired. One or more of the walls 264, 266 (or other walls if utilized) may be optically transparent to allow light to pass therethrough.

Figure 18:
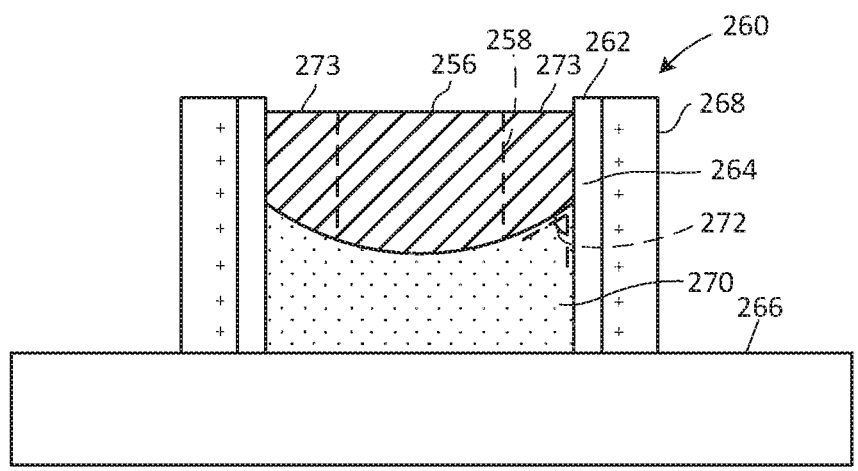
FIG. 18 illustrates a side cross sectional view of the fluid chamber shown in FIG. 17, with a portion of curable fluid fully or partially cured.

FIG. 18 illustrates the fluid chamber 260 in which the portion 258 of the curable fluid 256 has been fully or partially cured. The remaining portion 273 of the curable fluid, between the portion 258 and the side wall 264, is able to be shaped via an electrowetting process.

Figure 19:
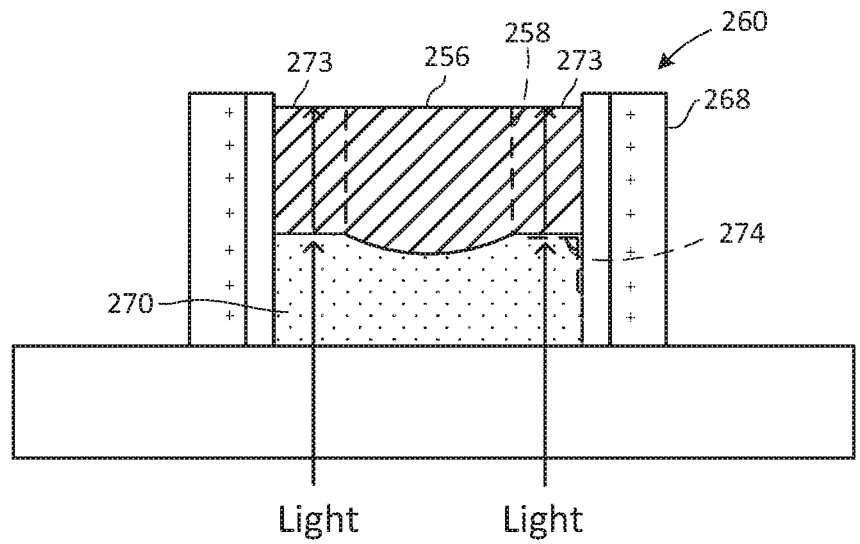
FIG. 19 illustrates a side cross sectional view of the fluid chamber shown in FIG. 17, with a remaining portion of the curable fluid being fully or partially cured.

FIG. 19 illustrates the fluid chamber 260 in which the surface shape of the remaining portion 273 of the curable fluid 256 is varied. The surface shape of the remaining portion 273 may be varied through the electrowetting process. For example, the voltage of the electrode 268 may be set to determine the shape of the surface of the portion of the curable fluid 256. The contact angle 274 of the curable fluid 256 may vary accordingly. In other embodiments, the natural shape of the remaining portion 273 of the curable fluid 256 in contact with the conductive fluid 270 may be utilized.

FIG. 19 illustrates the fluid chamber 260 in which light is applied to cure or partially cure the remaining portion 273 of the curable fluid 256. The shape of the surface of the remaining portion 273 may be set through the electowetting process. In one embodiment, the voltage of the electrode 268 may be maintained during the curing or partial curing of the remaining portion 273 of the curable fluid 256, to maintain the shape of the surface of the remaining portion 273.

Figure 20:
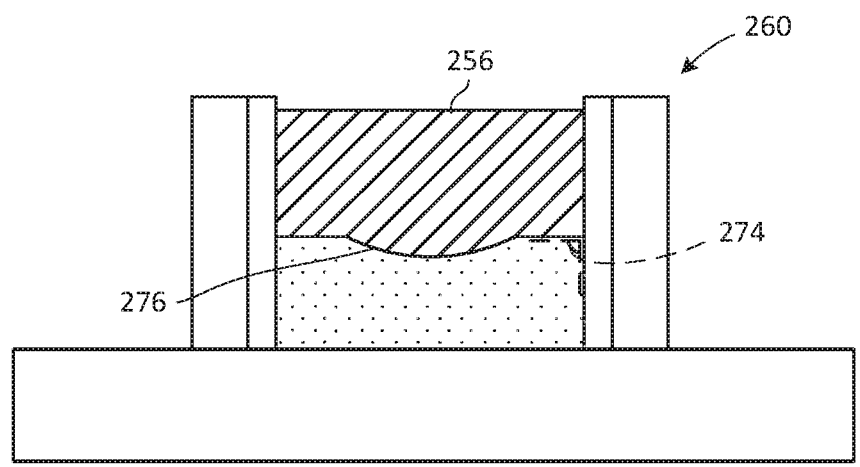
FIG. 20 illustrates a side cross sectional view of the fluid chamber shown in FIG. 17, with the curable fluid being partially or fully cured.

FIG. 20 illustrates the resulting surface 276 of the curable fluid 256 based on the curing of the curable fluid 256. The method described in regard to FIGS. 17-20 may be utilized to result in complex profiles for the surface 276 of the curable fluid, including aspheric shapes. A discontinuous shape may result. The resulting shape of the surface of the curable fluid 256 may vary from the shape shown in FIG. 20 in other embodiments.

In one embodiment, the method of FIGS. 17-20 may utilize a light intensity profile and/or an electrical excitation profile to determine the shape and intensity of the light being applied to the curable fluid, and/or the voltage of the electrode 268. Either of the light intensity profile or the electrical excitation profile may be used as a function of time.

In one embodiment, the method of FIGS. 17-20 may occur as a continuous cure (due to light) from the center of the fluid chamber 260 to the periphery. As the continuous cure is occurring, the contact angle of the curable fluid 256 may be varied as desired via an electrowetting process to produce the desired resulting shape of the curable fluid 256.

In one embodiment, the method of FIGS. 17-20 may occur as a zonal curing system, in which a central zone of the curable fluid is cured or partially cured, to produce a shape of the surface of the central zone. A zone positioned radially outward (which may be concentric) from the central zone may then have its surface shaped through electrowetting, and may then have light radiated upon it to produce a shape of the surface of this zone. An iterative process of shaping and curing may occur to consecutive zones positioned radially outward from the prior cured zone, until the entirety of the curable fluid is cured or partially cured. The iterative process may occur continuously in one embodiment, from the center zone to the periphery while modifying the contact angle. In one embodiment, the iterative process may occur in stages, from the center zone to the periphery while modifying the contact angle.

In one embodiment, the method described in regard to FIGS. 17-20 may be operated by a controller, such as controller 36. The controller may be configured to operate the light source 92 to produce the desired curing profile.

As an additional embodiment, when the curable fluid discussed in this application (for example curable fluid 12 or 74) is partly cured, the curing process may be stopped. The optical properties of the curable fluid may then be tested. Additional curing may occur to vary the optical properties of the curable fluid as desired. For example, if the curable fluid is cured through light, the optical properties of the curable fluid may be tested, and selective exposure to light, such as a light pattern discussed previously may occur. The selective exposure to light may vary the optical properties of the curable fluid to a desired state. This operation may be similar to the operation of a light adjustable intraocular lens, in which selective exposure to light may vary the local density of the curable fluid and cause shape variations at that location (e.g., due to migration of monomers to the dense areas). After the shape variations occur, the resulting lens may then be fully cured by radiating light upon the entirety of the lens. Multiple tests and shape corrections may occur prior to the lens being fully cured.

In one embodiment, the optical properties of the curable fluid may be tested prior to the start of a curing process. The optical properties of the curable fluid may be tested through optical testing methods, such as a Hartmann-Shack sensor test or a refractive method such as magnification testing. Other optical testing methods may be used as desired. A sensor 94 may be used to perform any of the optical testing methods. The sensor 94 may comprise an optical sensor or other form of sensor. In other embodiments, the optical testing methods may be performed without use of the sensor 94.

In one embodiment, the optical testing method may take place while the curable fluid remains in the fluid chamber. One or more of the walls of the fluid chamber or walls of the intraocular lens base may be optically transparent to allow optical testing of the curable fluid while the curable fluid remains in the fluid chamber. The sensor 94 may perform the optical testing method while the curable fluid remains in the fluid chamber.

The optical testing method may occur as the shape of the surface of the curable fluid is varied, in order to determine whether the surface is attaining the desired shape. The shape of the surface of the curable fluid may be varied through an electrowetting process, discussed previously. The optical testing method may occur prior, during, or after, the electrowetting process. The results of the optical testing method may be provided to the controller 36 as feedback, for the controller 36 to determine if the desired shape of the curable fluid is met. The feedback may be provided by the sensor 94.

In one embodiment, the optical testing method may occur after a curing process has begun. Multiple tests and shape corrections may occur after a curing process has begun. The shape corrections may occur through an electrowetting process, or through selective exposure to light as discussed previously. The results of the optical testing method may be provided to the controller 36 as feedback, for the controller 36 to determine if the desired shape of the curable fluid is met. The feedback may be provided by the sensor 94.

In one embodiment, the optical testing method may occur after the intraocular lens has been implanted in a patient's eye. Based on the testing processes, additional shape correction to the intraocular lens may occur based on selective exposure to light as discussed previously. The light source 92 may be configured to expose the intraocular lens to light when it is in the patient's eye. After the shape variations occur, the intraocular lens may then be fully cured by radiating light upon the entirety of the lens. The results of the optical testing method may be provided to the controller 36 as feedback, for the controller 36 to determine if the desired shape of the curable fluid is met. The feedback may be provided by the sensor 94.

In one embodiment, the controller 36 may be configured to operate the optical testing methods. The controller 36 may be configured to operate the sensor 94 to perform the optical testing methods. The controller 36 may be configured to determine, based on feedback from the optical method, whether the desired shape of the surface of the curable fluid is met. The controller 36 may be configured to produce additional shape corrections to the curable fluid to achieve the desired shape of the curable fluid surface, which may include corrections through control of one or more electrodes in an electrowetting process, or corrections through the light source 92 with exposure to light. The resulting desired shape of the lens surface and/or the steps to produce the desired shape may be stored in the memory of the controller 36 and effected by the processor to produce the desired shape.

The apparatuses, systems, and methods disclosed herein may result in a variety of shapes of one or more surfaces of a lens or portion of a lens, such shapes including concave, convex, planar, toric, or aspheric, or other shapes as desired.

The functions of the controller 36, light source 92, and/or feedback system disclosed herein may be used with any embodiment disclosed herein.

The apparatuses, systems, and methods disclosed herein may result in improved manufacturing methods for ophthalmic lenses, which may be produced locally with an optical practitioner.

Any of the apparatuses, systems, and methods disclosed herein may be interchanged and/or combined as desired.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary. The terms "approximate[ly]" and "substantial[ly]" represent an amount that may vary from the stated amount, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A system comprising:
   a fluid chamber having an interior surface;
   a conductive fluid positioned in the fluid chamber and contacting the interior surface at a contact angle;
   a curable fluid positioned in the fluid chamber and being immiscible with the conductive fluid, the curable fluid having a surface with a shape, the surface of the curable fluid facing the conductive fluid, and the shape of the surface of the curable fluid being dependent on the contact angle of the conductive fluid with the interior surface;
   one or more electrodes configured to vary a voltage between the conductive fluid and at least one of the one or more electrodes to thereby vary the contact angle and the shape of the surface of the curable fluid;
   a feedback system configured to allow feedback on optical properties of the surface of the curable fluid that result from the voltage of the one or more electrodes, wherein the feedback system includes a wavefront sensor to measure said optical properties to determine whether they meet desired optical properties; and
   a light source configured to at least partially cure the curable fluid when the curable fluid is positioned in the fluid chamber, wherein the system is configured to radiate light to cure or partially cure a portion of the curable fluid, and, subsequent to curing or partially curing a portion of the curable fluid, to vary the surface shape of a remaining portion of the curable fluid and to apply light to cure or partially cure the remaining portion of the curable fluid.

2. The system of claim 1, wherein the conductive fluid comprises water.

3. The system of claim 1, wherein the curable fluid includes at least one of silicone monomers or acrylic monomers.

4. The system of claim 1, wherein the one or more electrodes are configured to vary a wettability of the interior surface to thereby vary the contact angle and the shape of the surface of the curable fluid.

5. The system of claim 1, wherein:
   the interior surface forms at least a portion of a side wall of the fluid chamber; and a bottom of the fluid chamber is bounded by an end wall.

6. The system of claim 1, wherein:
   the conductive fluid is a first conductive fluid;
   a second conductive fluid is positioned in the fluid chamber; and
   the curable fluid is sandwiched between the first conductive fluid and the second conductive fluid and has a surface that faces the second conductive fluid.

7. A method comprising:
   providing a fluid chamber having an interior surface, the fluid chamber including a conductive fluid and a curable fluid therein, the curable fluid having a surface that faces the conductive fluid and that has a shape;
   varying the shape of the surface of the curable fluid by varying a wettability of the interior surface;
   curing or partially curing a portion of the curable fluid by radiating with light;
   using a feedback system with a wavefront sensor to measure optical properties of the surface of the curable fluid to determine whether the measured optical properties meet desired optical properties;
   subsequent to curing or partially curing a portion of the curable fluid, varying the surface shape of a remaining portion of the curable fluid; and applying light to cure or partially cure the remaining portion of the curable fluid.

8. The method of claim 7, wherein the varying of the wettability of the interior surface includes varying a voltage between the conductive fluid and one or more electrodes.

9. The method of claim 7, wherein the at least partial curing of the curable fluid includes at least partially curing the curable fluid while the curable fluid is positioned within the fluid chamber.

10. The method of claim 7, wherein the at least partial curing of the curable fluid produces a surface of an ophthalmic lens from the surface of the curable fluid.

11. The method of claim 7, wherein the curable fluid includes at least one of silicone monomers or acrylic monomers.

12. The method of claim 7, wherein:
the conductive fluid is a first conductive fluid,
a second conductive fluid is positioned in the fluid chamber, and
the curable fluid is sandwiched between the first conductive fluid and the second conductive fluid and has a surface that faces the second conductive fluid; and
the method further comprises:
varying a shape of the surface of the curable fluid that faces the second conductive fluid by varying a wettability of the interior surface.

13. A method comprising:
providing a fluid chamber that is positioned upon at least a portion of an intraocular lens, the fluid chamber including a conductive fluid and a curable fluid therein, the conductive fluid and the curable fluid being immiscible and being separated at an interface, the curable fluid being in contact with the at least the portion of the intraocular lens;
varying a shape of the interface by varying a voltage between the conductive fluid and one or more electrodes;
curing or partially curing a portion of the curable fluid by radiating with light when the curable fluid is in contact with the at least the portion of the intraocular lens;
using a feedback system with a wavefront sensor to measure optical properties of the surface of the curable fluid to determine whether the measured optical properties meet desired optical properties;
subsequent to curing or partially curing a portion of the curable fluid, varying the shape of a remaining portion of the curable fluid; and applying light to cure or partially cure the remaining portion of the curable fluid.

14. The method of claim 13, wherein the at least partial curing of the curable fluid occurs when the curable fluid is in contact with a surface of the intraocular lens that is in an optical zone of the intraocular lens.

15. The method of claim 14, wherein the surface of the intraocular lens is opposite a surface of the intraocular lens that is planar.

16. The method of claim 14, wherein the surface of the intraocular lens is opposite a surface of the intraocular lens that includes a lens surface.

17. The method of claim 13, wherein the varying of the shape of the interface includes producing at least one of a convex shape, a concave shape, a toric shape, or an aspheric shape for the shape of the interface.

* * * * *